United States Patent
Peterson et al.

(10) Patent No.: US 10,787,512 B2
(45) Date of Patent: Sep. 29, 2020

(54) MELATONIN MONOCLONAL ANTIBODY, DETECTION, METHODS AND USES THEREOF

(71) Applicant: SALIMETRICS, LLC, State College, PA (US)

(72) Inventors: Jon Eric Peterson, Bellefonte, PA (US); Daming Li, State College, PA (US); Xiuwen Liu, Millbrae, CA (US); Meng-Yun Sandy Chou, Foster City, CA (US); Howard Paul Sard, Arlington, MA (US)

(73) Assignee: SALIMETRICS, LLC, State College, PA (US)

( * ) Notice: Subject to any disclaimer, the term of this patent is extended or adjusted under 35 U.S.C. 154(b) by 154 days.

(21) Appl. No.: 14/775,351

(22) PCT Filed: Mar. 14, 2014

(86) PCT No.: PCT/US2014/029257
§ 371 (c)(1),
(2) Date: Sep. 11, 2015

(87) PCT Pub. No.: WO2014/144725
PCT Pub. Date: Sep. 18, 2014

(65) Prior Publication Data
US 2016/0053009 A1 Feb. 25, 2016

Related U.S. Application Data

(60) Provisional application No. 61/809,751, filed on Apr. 8, 2013, provisional application No. 61/794,713, filed on Mar. 15, 2013.

(51) Int. Cl.
*C07K 16/26* (2006.01)
*C07K 17/00* (2006.01)
*C07D 209/14* (2006.01)
*G01N 33/74* (2006.01)

(52) U.S. Cl.
CPC ............ *C07K 16/26* (2013.01); *C07D 209/14* (2013.01); *C07K 17/00* (2013.01); *G01N 33/74* (2013.01); *C07K 2317/20* (2013.01); *C07K 2317/21* (2013.01); *C07K 2317/24* (2013.01); *C07K 2317/56* (2013.01); *C07K 2317/565* (2013.01); *C07K 2317/92* (2013.01); *G01N 2333/575* (2013.01)

(58) Field of Classification Search
None
See application file for complete search history.

(56) References Cited

FOREIGN PATENT DOCUMENTS

WO 2003066830 A2 8/2004
WO WO-2012149356 A2 * 11/2012 ......... C07K 16/2878
WO WO 2012149356 A2 * 11/2012 ......... C07K 16/2878

OTHER PUBLICATIONS

Becker-Andre. Pineal gland hormone melatonin binds and activates an orphan of the nuclear receptor superfamily. Journal of Biological Chemistry, 1994; 269(46):28531-28534.*
Paul (Fundamental Immunology, 3rd Edition, Raven Press, New York, Chapter 8, pp. 292-295, 1993).*
MacCallum et al. Antibody-antigen Interactions: Contact Analysis and Binding Site Topography. Journal of Molecular Biology, 262:732-745, 1996.*
Casset et al. A peptide mimetic of an anti-CD4 monoclonal antibody by rational design. Biochemical and Biophysical Research Communications, 307:198-205, 2003.*
Vajdos et al. Comprehensive Functional Maps of the Antigen-binding Site of an Anti-ErbB2 Antibody Obtained with Shotgun Scanning Mutagenesis. Journal of Molecular Biology, Jul. 5, 2002;320(2):415-28.*
Brown et al. Tolerance to Single, but Not Multiple, Amino Acid Replacements in Antibody VH CDR2. Journal of Immunology. May 1996; 156(9):3285-91.*
Rudikoff et al. Single amino acid substitution altering antigen-binding specificity. Proc. Natl. Acad. Sci. USA, 79(6):1979-1983, Mar. 1982.*
Colman. Effects of amino acid sequence changes on antibody-antigen interactions. Research in Immunology, 145:33-36, 1994.*
Paul. Fundamental Immunology, 3rd Edition, Raven Press, New York, Chapter 8, pp. 292-295, 1993 (Year: 1993).*
MacCallum et al. Journal of Molecular Biology, 262:732-745, 1996 (Year: 1996).*
Casset et al. Biochemical and Biophysical Research Communications, 307:198-205, 2003 (Year: 2003).*
Vajdos et al. (Journal of Molecular Biology, Jul. 5, 2002;320(2):415-28 (Year: 2002).*
Brown et al. Journal of Immunology. May 1996; 156(9):3285-91 (Year: 1996).*
Rudikoff et al. Proc. Natl. Acad. Sci. USA, 79(6):1979-1983, Mar. 1982 (Year: 1982).*
Colman. Research in Immunology, 145:33-36, 1994 (Year: 1994).*
Bowie et al. Science, 1990, 247:1306-1310 (Year: 1990).*
Burgess et al. J. Cell Biol. 111:2129-2138, 1990 (Year: 1990).*
Lazar et al. Mol. Cell. Biol., 8:1247-1252, 1988 (Year: 1988).*
Bork. Genome Research, 2000,10:398-400 (Year: 2000).*
Soukhtanloo, M. et al., Preparation and Characterization of Monoclonal Antibody Against Melatonin, Hybridoma, 2008, 27(3):205-209.

(Continued)

Primary Examiner — Vanessa L. Ford
Assistant Examiner — Sandra E Dillahunt
(74) Attorney, Agent, or Firm — Pillsbury Winthrop Shaw Pittman, LLP

(57) ABSTRACT

The invention provides monoclonal antibodies and fragments thereof that specifically bind to melatonin. Also provided are heavy chain variable region (VH) and light chain variable region (VL) sequences of such monoclonal antibodies and fragments thereof. Further provided are melatonin conjugates, and methods and uses, for example, determining, detecting, measuring, screening for, analyzing and monitoring an amount of melatonin in a sample.

20 Claims, 10 Drawing Sheets

Specification includes a Sequence Listing.

(56) References Cited

OTHER PUBLICATIONS

Yang, T., et al., Preparation and Identification of Anti-Melatonin Monoclonal Antibodies, Journal of Pineal Research, 2006, 40(4):350-354.
Dreher, K.L.et al., cDNA Clone Encoding a Complete Rabbit Immunoglobulin Kappa Light Chain of b4 Allotype: Ig Kappa Chain b4, Partial [Oryctolagus cuniculus]: GenBank Accession No. AAB59259.1. Oct. 19, 1997.
Lopez-Maques, RL, Occurrence of Proton Translocating Pyrophosphatases in Photosynthetic Protists: Proton-Translocating Inorganiz Pyrophosphatase, Partical [Isochrysis galbana]: GenBank: Acession No. CAH58672.1.
Popkov, M. et al., Rabbit Immune Repertiores as Sources for Therapeutic Monoclonal Antiboes: The Impact of Kappa Allotype-Correlated Variation in Cysteine Content on Antibody Libraries Selected by Phage Display: GenBankAcession No. AA006444.1 Dec. 26, 2002.
Rhee, K.J. et al., Role of Comensal Bacterial in Development of Gut-Associated Lymphoid Tissues and Preimmune Antibody Preperiore: Immunoglobulin Heavy Chain VDJ Region, Partial []ryctolagus cuniculus]: GenBank Accession No. AAR91809.1. Jan. 18, 2004.
Sehgal, D. et al., Generation of the Primary Antibody Repertiore in Rabbits: Expression of a Diverse Set of IgK-V Genes May Compensate for Limited Cbominatorial Divesity at the Heavy Chain Locus: GenBank: Accession No. AAF14424.1 Dec. 2, 1999.
Venables, J.P. et al., EASI—Enrichment of alternatively Splied Isoforms: p53-Ex(2-4) Isoform, Partial [*Homo sapiens*]: GenBank Accession No. ABG49481.1 Sep. 25, 2006.
Winstead, C.R. et al, Antigen-Induced Somatic Diversification of Rabbit IgH Genes: Gene Conversion and Point Mutation: Oryctolagus cuniculus Clone 20A6.23 Immunoglobulin Heavy Chain VDJ Region (IgH) mRNA, Partial cds: GenBank Accession No. AF098236.1. Sep. 14, 2001.
Winstead, C.R. et al, Antigen-Induced Somatic Diversification of Rabbit IgH Genes: Gene Conversion and Point Mutation: Oryctolagus cuniculus Clone 8.2-2 Immunoglobulin Light Chain VJ Kappa Region (IgL) mRNA, Partial cds: GenBank Accession No. AF098240.1. Sep. 14, 2001.
Winstead, C.R. et al, Antigen-Induced Somatic Diversification of Rabbit IgH Genes: Gene Conversion and Point Mutation: Immunoglobulin Heavy Chain VDJ Region, Partial [Oryctolagus cuniculus]: GenBank: AAF22692.1. Sep. 14, 2001.
Young, N.D. et al., The Genome Sequence of the Model Legume, *Medicago truncatula*: DGSL Esteras/Lipase [*Medicaog truncatula*]: NCBI Reference Sequence: XP_003637203.1. Nov. 29, 2011.
Kawa, S., et al., The improvement of an anti-CD22 immunotoxin conversion to single-chain and disulfide stabilized form and affinity maturation by alanine scan, 2011, mAbs, 3:5:479-486.
Kuan, C-T, et al., Affinity-matured anti-glycoprotein NMB recombinant immunotoxins targeting malignant gliomas and melanomas, 2011, Int. J. Cancer, 129(1):111-121.
Votsmeier, C., et al., Femtomolar Fab binding affinities to a protein target by alternative CDR residue co-optimization strategies without phage or cell surface display, 2012, mAbs, 4:3:341-348.
European Patent Office, Office Action for EP Patent Application No. 14764194.8, dated Jul. 12, 2018, pp. 1-6.
Du et al., Molecular Basis of Recognition of human Osteopontin by 23C3, a Potential Therapeutic Antibody for Treatment of Rheumatoid Arthritis, Journal of Molecular Biology, Oct. 17, 2008, pp. 835-842, vol. 382(4), Academic Press, United Kindom.
Caldas et al., Humanization of the anti-CD18 antibody 6.7: an unexpected effect of a framework residue in binding to antigen, Molecular Immunologic, May 1, 2003, pp. 941-952, vol. 39(15).

* cited by examiner

FIGURE 2

SLM-1-76-11-Heavy Chain Coding Nucleotide Sequence (Shaded Area - variable region)

ATGGAGACTGGGCTGCGCTGGCTTCTCCTGGTCGCTGTGCTCAAAGGTGTCCAGTGTCAGTCGTTGGAGGAG
TCCGGGGGAGACCTGGTCAAGCCTGGGGGCATCCCTGACACTCACCTGCACAGCCTCTGGATTCTCTTTTAGT
CGCTATGATTATATGTGCTGGGTCCGCCAGGCTCCAGGGAAGGGGCTGGAGTGGATCGCAAGTATTTATGTT
GGTAGTGGTGTCACTTACTACTCGACCTGGGCGAGAGGCCGATTCGCCATCTCCCAAACCTCGTCGACCACG
ATGACTCTACAAATGACCAGTCTGACAGCCGCGGACACGGCCACTTACTTCTGTGCGAGATTTCATGGTCAT
GGTGGTGGTGATTATGCTCTGGGGGCTTTTGATCCCTGGGGCCCAGGCACCCTGGTCACCGTCTCCTCAGGG
CAACCTAAGGCTCCATCAGTCTTCCCACTGGCCCCCTGCTGCGGGGACACACCCAGCTCCACGGTGACCCTG
GGCTGCCTGGTCAAAGGGTACCT

VH

CDR-H1
METGLRWLLLVAVLKGVQCQSLEESGGDLVKPGASLTLTCTASGFSFS<u>RYDYMC</u>WVRQAPGKGLEWIA
    CDR-H2                                                      CDR-H3
<u>SIYVGSGVTYYSTWAR</u>GRFAISQTSSTTMTLQMTSLTAADTATYFCAR<u>FHGHGGGDYALGAFDP</u>WGPGTLVT
VSS

VC (CH)

GQPKAPSVFPLAPCCGDTPSSTVTLGCLVKGY

SLM-1-76-11-Light Chain Coding Nucleotide Sequence (Shaded Area - variable region)

ATGGACACGAGGGCCCCCACTCAGCTGCTGGGGCTCCTGCTGCTCTGGCTCCCAGGTGCCAGATGTGCCTAT
GATATGACCCAGACTCCAGCCTCCGTGTCTGCAGCTGTGGGAGGCACAGTCACCATCAATTGCCAGGCCAGT
CAGAGCATCAGCAACCTCTTAGCCTGGTATCAGCAGAAACCAGGGCAGCCTCCCAAGCTCCTGATCTATTCT
GCATCCACTCTGGCATCTGGGGTCCCATCGCGGTTCAAAGGCAGTGGATCTGGGACACAGTTCACTCTCACC
ATCAGCGACCTGGAGTGTGCCGATGCTGCCACTTACTACTGTCAGCAGGGTTATGATGGTATTGGTGTTGTA
AATTTTTTCGGCGGAGGGACCGAGGTGGTGGTCAAAGGTGATCCAGTTGCACCTACTGTCCTCATCTTCCCA
CCAGCTGCTGATCAGGTGGCAACTGGAACAGTCACCATCGTGTGTGTGGCGAATAAATACTTTCCCGATGTC
ACCGTCACCTGGGAGGTGGATGGCACCACCCAAACAACTGGCATCGAGAACAGTAAAACACCGCAGAATTCT
GCAGATTGTACCTACAACCTCAGCAGCACTCTGACACTGACCAGCACACAGTACAACAGCCACAAAGAGTAC
ACCTGCAAGGTGACCCAGGGCACGACCTCAGTCGTCCAGAGCTTCAATAGGGGTGACTGT<u>TAG</u>

VL
                                                                      CDR-L1
MDTRAPTQLLGLLLLWLPGARCAYDMTQTPASVSAAVGGTVTINC<u>QASQSISNLLA</u>WYQQKPGQPPKLL
  CDR-L2                                                   CDR-L3
IY<u>SASTLAS</u>GVPSRFKGSGSGTQFTLTISDLECADAATYYC<u>QQGYDGIGVVNF</u>FGGGTEVVVK

VC (CL)

GDPVAPTVLIFPPAADQVATGTVTIVCVANKYFPDVTVTWEVDGTTQTTGIENSKTPQNSADCTYNLSSTLT
   LT
STQYNSHKEYTCKVTQGTTSVVQSFNRGDC

FIGURE 2 CONTINUED

[SEQ ID NO. 1]:
ATGGAGACTGGGCTGCGCTGGCTTCTCCTGGTCGCTGTGCTCAAAGGTGTCCAGTGTCAGTCGTTGGAGGAGTCCGGGGGAGACCTGGTC
AAGCCTGGGGCATCCCTGACACTCACCTGCACAGCCTCTGGATTCTCTTTTAGTCGCTATGATTATATGTGCTGGGTCCGCCAGGCTCCA
GGGAAGGGGCTGGAGTGGATCGCAAGTATTTATGTTGGTAGTGGTGTCACTTACTACTCGACCTGGGCGAGAGGCCGATTCGCCATCTCC
CAAACCTCGTCGACCACGATGACTCTACAAATGACCAGTCTGACAGCCGCGGACACGGCCACTTACTTCTGTGCAGATTTCATGGTCAT
GGTGGTGGTGATTATGCTCTGGGGGCTTTTGATCCCTGGGGCCCAGGCACCCTGGTCACCGTCTCCTCA

[SEQ ID NO. 2]:   CGCTATGATTATATGTGC

[SEQ ID NO. 3]:   AGTATTTATGTTGGTAGTGGTGTCACTTACTACTCGACCTGGGCGAGAGGC

[SEQ ID NO. 4]:   TTTCATGGTCATGGTGGTGGTGATTATGCTCTGGGGGCTTTTGATCCC

[SEQ ID NO. 5]:
GGGCAACCTAAGGCTCCATCAGTCTTCCCACTGGCCCCCTGCTGCGGGGACACACCCAGCTCCACGGTGACCCTGGGCTGCCTGGTCAAA
GGGTACCT

[SEQ ID NO. 6]:
METGLRWLLLVAVLKGVQCQSLEESGGDLVKPGASLTLTCTASGFSFSRYDYMCWVRQAPGKGLEWIASIYVGSGVTYYSTWARGRFAIS
QTSSTTMTLQMTSLTAADTATYFCARFHGHGGDYALGAFDPWGPGTLVTVSS

[SEQ ID NO. 7]:   RYDYMC

[SEQ ID NO. 8]:   SIYVGSGVTYYSTWARG

[SEQ ID NO. 9]:   FHGHGGDYALGAFDP

[SEQ ID NO. 10]:  GQPKAPSVFPLAPCCGDTPSSTVTLGCLVKGY

[SEQ ID NO. 11]:
ATGGACACGAGGGCCCCCACTCAGCTGCTGGGGCTCCTGCTGCTCTGGCTCCCAGGTGCCAGATGTGCCTATGATATGACCCAGACTCCA
GCCTCCGTGTCTGCAGCTGTGGGAGGCACAGTCACCATCAATTGCCAGGCCAGTCAGAGCATCAGCAACCTCTTAGCCTGGTATCAGCAG
AAACCAGGGCAGCCTCCCAAGCTCCTGATCTATTCTGCATCCACTCTGGCATCTGGGGTCCCATCGCGGTTCAAAGGCAGTGGATCTGGG
ACACAGTTCACTCTCACCATCAGCGACCTGGAGTGTGCCGATGCTGCCACTTACTACTGTCAGCAGGGTTATGATGGTATTGGTGTTGTA
AATTTTTCGGCGGAGGGACCGAGGTGGTGGTCAAA

[SEQ ID NO. 12]:  CAGGCCAGTCAGAGCATCAGCAACCTCTTAGCC

[SEQ ID NO. 13]:  TCTGCATCCACTCTGGCATCT

[SEQ ID NO. 14]:  CAGCAGGGTTATGATGGTATTGGTGTTGTAAATTTT

[SEQ ID NO. 15]:
GGTGATCCAGTTGCACCTACTGTCCTCATCTTCCCACCAGCTGCTGATCAGGTGGCAACTGGAACAGTCACCATCGTGTGTGTGGCGAAT
AAATACTTTCCCGATGTCACCGTCACCTGGGAGGTGGATGGCACCACCCAAACAACTGGCATCGAGAACAGTAAAACACCGCAGAATTCT
GCAGATTGTACCTACAACCTCAGCAGCACTCTGACACTGACCAGCACACAGTACAACAGCCACAAAGAGTACACCTGCAAGGTGACCCAG
GGCACGACCTCAGTCGTCCAGAGCTTCAATAGGGGTGACTGTTAG

[SEQ ID NO. 16]:
MDTRAPTQLLGLLLLWLPGARCAYDMTQTPASVSAAVGGTVTINCQASQSISNLLAWYQQKPGQPPKLLIYSASTLASGVPSRFKGSGS
GTQFTLTISDLECADAATYYCQQGYDGIGVVNFGGGTEVVVK

[SEQ ID NO. 17]:  QASQSISNLLA

[SEQ ID NO. 18]:  SASTLAS

[SEQ ID NO. 19]:  QQGYDGIGVVNF

[SEQ ID NO. 20]:
GDPVAPTVLIFPPAADQVATGTVTIVCVANKYFPDVTVTWEVDGTTQTTGIENSKTPQNSADCTYNLSSTLTLTSTQYNSHKEYTCKVTQ
GTTSVVQSFNRGDC

FIGURE 4A
| Sam ID | Time (hrs) | Mean (pg/ml) | SD |
|---|---|---|---|
| C-3 | 4.0 | 3.3 | 0.09 |
| C-4 | 3.5 | 4.8 | 0.96 |
| C-5 | 3.0 | 4.4 | 0.79 |
| C-6 | 2.5 | 6.8 | 0.26 |
| C-7 | 2.0 | 9.4 | 0.82 |
| C-8 | 1.5 | 13.5 | 0.39 |
| C-9 | 1.0 | 15.7 | 0.53 |
| C-10 | 0.5 | 16.3 | 0.07 |
| C-11 | 0.0 | 18.9 | 1.24 |
| C-12 | -0.5 | 20.5 | 0.22 |
| C-13 | -1.0 | 24.2 | 2.07 |
2 SD+Baseline = 5.73
DLMO = 2.71 hrs
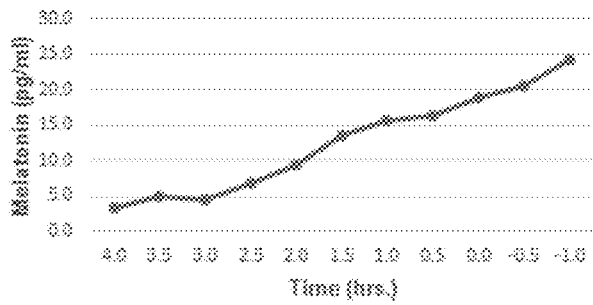
| Sam ID | Time (hrs) | Mean (pg/ml) | SD |
|---|---|---|---|
| C-3 | 4.0 | 3.1 | 1.66 |
| C-4 | 3.5 | 5.2 | 0.86 |
| C-5 | 3.0 | 8.4 | 0.42 |
| C-6 | 2.5 | 28.5 | 9.97 |
| C-7 | 2.0 | 36.9 | 9.40 |
| C-8 | 1.5 | 50.0 | 0.00 |
| C-9 | 1.0 | 50.0 | 0.00 |
| C-10 | 0.5 | 50.0 | 0.00 |
| C-11 | 0.0 | 50.0 | 0.00 |
| C-12 | -0.5 | 50.0 | 0.00 |
| C-13 | -1.0 | 50.0 | 0.00 |
2 SD+Baseline = 10.94
DLMO = 2.94 hrs
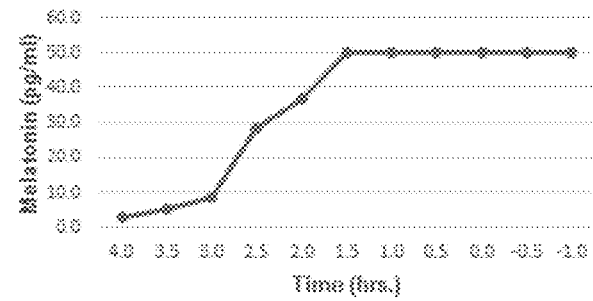
| Sam ID | Time (hrs) | Normalized Salimetrics | Normalized Bühlmann |
|---|---|---|---|
| C-3 | 4.0 | 0.26 | 0.09 |
| C-4 | 3.5 | 0.39 | 0.15 |
| C-5 | 3.0 | 0.35 | 0.24 |
| C-6 | 2.5 | 0.54 | 0.82 |
| C-7 | 2.0 | 0.75 | 1.06 |
| C-8 | 1.5 | 1.08 | 1.44 |
| C-9 | 1.0 | 1.25 | 1.44 |
| C-10 | 0.5 | 1.30 | 1.44 |
| C-11 | 0.0 | 1.51 | 1.44 |
| C-12 | -0.5 | 1.64 | 1.44 |
| C-13 | -1.0 | 1.93 | 1.44 |
| DLMO = | | 0.46 | 0.32 |
(Red shading shows approximate DLMO time before final calculation)
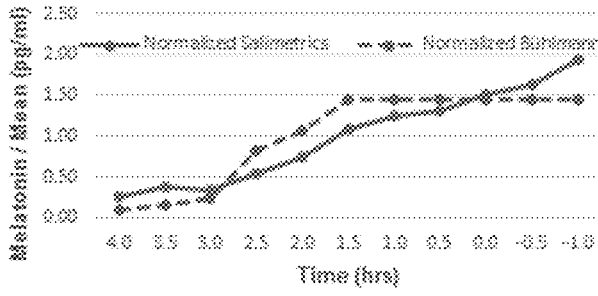

FIGURE 4B
| Sam ID | Time (hrs) | Mean (pg/ml) | SD |
|---|---|---|---|
| D-3 | 4.0 | 1.4 | 0.55 |
| D-4 | 3.5 | 2.1 | 0.08 |
| D-6 | 2.5 | 2.8 | 0.33 |
| D-7 | 2.0 | 4.6 | 0.13 |
| D-8 | 1.5 | 6.9 | 0.23 |
| D-9 | 1.0 | 8.76 | 0.18 |
| D-10 | 0.5 | 13.7 | 0.76 |
| D-11 | 0.0 | 12.5 | 0.51 |
| D-12 | -0.5 | 13.9 | 0.14 |
| D-13 | -1.0 | 11.6 | 0.00 |
| | 2 SD+Baseline = | 2.73 | |
| | DLMO = | 3.43 hrs | |
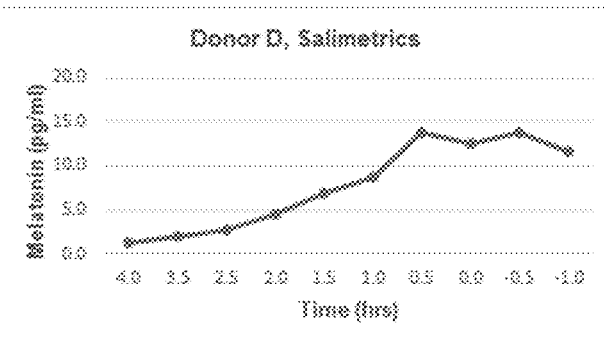
| Sam ID | Time (hrs) | Mean (pg/ml) | SD |
|---|---|---|---|
| D-3 | 4.0 | 1.6 | 0.16 |
| D-4 | 3.5 | 2.7 | 0.04 |
| D-6 | 2.5 | 11.6 | 0.61 |
| D-7 | 2.0 | 19.1 | 0.54 |
| D-8 | 1.5 | 50.0 | 0.00 |
| D-9 | 1.0 | 50.0 | 0.00 |
| D-10 | 0.5 | 50.0 | 0.00 |
| D-11 | 0.0 | 50.0 | 0.00 |
| D-12 | -0.5 | 50.0 | 0.00 |
| D-13 | -1.0 | 50.0 | 0.00 |
| | 2 SD+Baseline = | 3.63 | |
| | DLMO = | 3.04 hrs | |
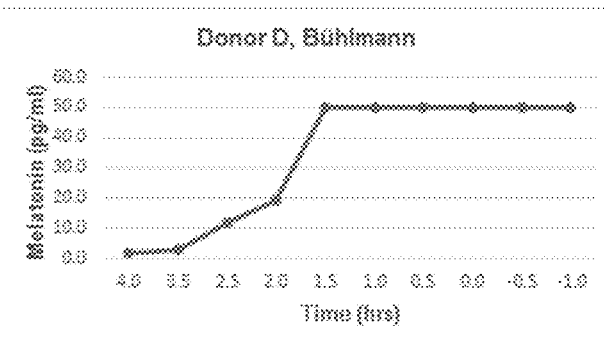
| Sam ID | Time (hrs) | Normalized Salimetrics | Normalized Bühlmann |
|---|---|---|---|
| D-3 | 4.0 | 0.18 | 0.05 |
| D-4 | 3.5 | 0.27 | 0.09 |
| D-6 | 2.5 | 0.36 | 0.37 |
| D-7 | 2.0 | 0.60 | 0.61 |
| D-8 | 1.5 | 0.90 | 1.60 |
| D-9 | 1.0 | 1.14 | 1.60 |
| D-10 | 0.5 | 1.78 | 1.60 |
| D-11 | 0.0 | 1.62 | 1.60 |
| D-12 | -0.5 | 1.80 | 1.60 |
| D-13 | -1.0 | 1.50 | 1.60 |
| | DLMO = | 0.35 | 0.12 |
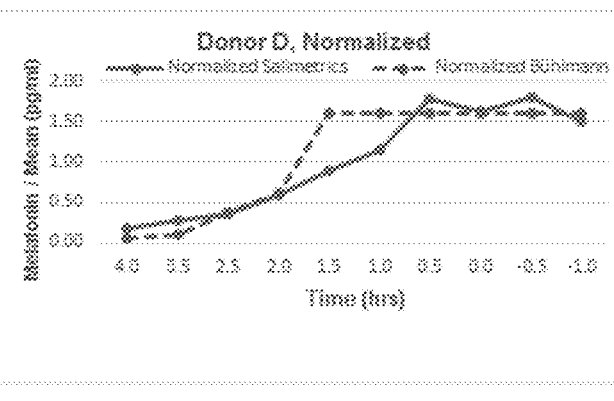
(Red shading shows approximate DLMO time before final calculation)

FIGURE 4C
| Sam ID | Time (hrs) | Mean (pg/ml) | SD |
|---|---|---|---|
| F-1 | 5.0 | 1.6 | 0.27 |
| F-2 | 4.5 | 1.5 | 0.04 |
| F-3 | 4.0 | 1.4 | 0.13 |
| F-4 | 3.5 | 2.3 | 0.38 |
| F-5 | 3.0 | 2.7 | 0.29 |
| F-6 | 2.5 | 3.7 | 0.18 |
| F-7 | 2.0 | 5.8 | 0.54 |
| F-8 | 1.5 | 6.6 | 0.13 |
| F-9 | 1.0 | 12.0 | 0.72 |
| F-10 | 0.5 | 12.6 | 0.38 |
| F-11 | 0.0 | 16.8 | 0.67 |
| F-12 | -0.5 | 17.4 | 0.07 |
| F-13 | -1.0 | 19.3 | 0.60 |
2 SD+Baseline = 1.71
DLMO = 3.82 hrs
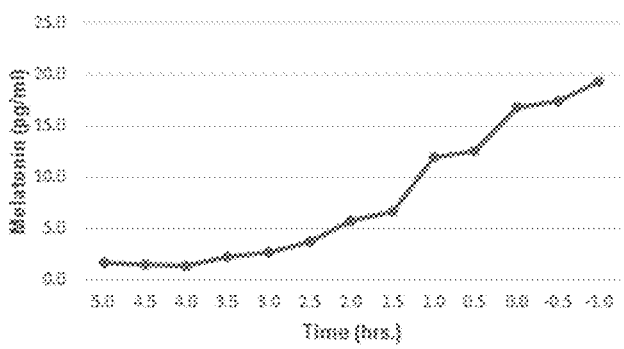
| Sam ID | Time (hrs) | Mean (pg/ml) | SD |
|---|---|---|---|
| F-1 | 5.0 | 2.3 | 0.23 |
| F-2 | 4.5 | 2.5 | 0.12 |
| F-3 | 4.0 | 2.1 | 0.13 |
| F-4 | 3.5 | 4.0 | 0.38 |
| F-5 | 3.0 | 6.4 | 0.22 |
| F-6 | 2.5 | 9.0 | 0.27 |
| F-7 | 2.0 | 24.0 | 0.38 |
| F-8 | 1.5 | 24.5 | 1.76 |
| F-9 | 1.0 | 24.5 | 1.37 |
| F-10 | 0.5 | 40.7 | 7.10 |
| F-11 | 0.0 | 44.0 | 8.42 |
| F-12 | -0.5 | 34.3 | 4.42 |
| F-13 | -1.0 | 40.6 | 11.34 |
2 SD+Baseline = 2.64
DLMO = 3.85 hrs
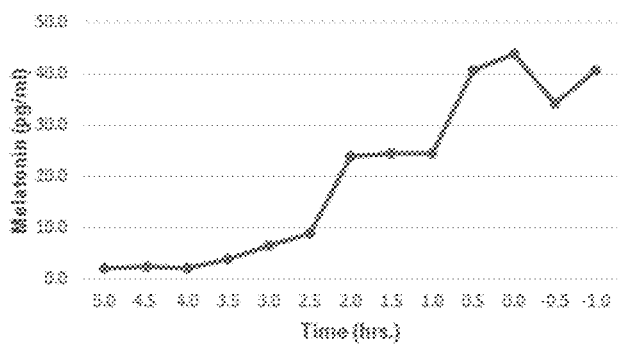
| Sam ID | Time (hrs) | Normalized Salimetrics | Normalized Buhlmann |
|---|---|---|---|
| F-1 | 5.0 | 0.20 | 0.11 |
| F-2 | 4.5 | 0.19 | 0.12 |
| F-3 | 4.0 | 0.17 | 0.10 |
| F-4 | 3.5 | 0.29 | 0.20 |
| F-5 | 3.0 | 0.33 | 0.32 |
| F-6 | 2.5 | 0.47 | 0.45 |
| F-7 | 2.0 | 0.72 | 1.21 |
| F-8 | 1.5 | 0.83 | 1.23 |
| F-9 | 1.0 | 1.51 | 1.23 |
| F-10 | 0.5 | 1.58 | 2.04 |
| F-11 | 0.0 | 2.11 | 2.21 |
| F-12 | -0.5 | 2.18 | 1.72 |
| F-13 | -1.0 | 2.42 | 2.04 |
DLMO = 0.22 | 0.13
(Red shading shows approximate DLMO time before final calculation)
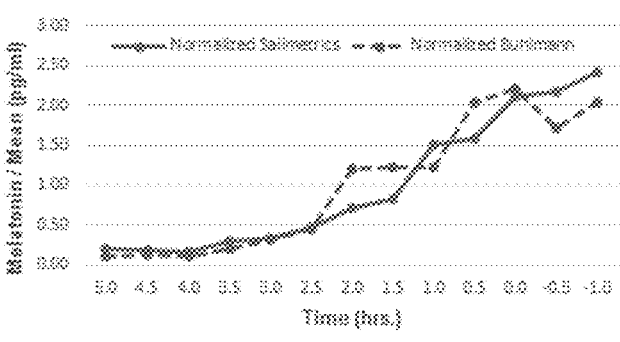

FIGURE 4D
| Sam ID | Time (hrs) | Mean (pg/ml) | SD |
|---|---|---|---|
| I-2 | 4.5 | 4.3 | 0.06 |
| I-3 | 4.0 | 2.8 | 0.01 |
| I-4 | 3.5 | 5.2 | 0.87 |
| I-6 | 2.5 | 5.8 | 0.21 |
| I-7 | 2.0 | 4.5 | 1.08 |
| I-8 | 1.5 | 7.1 | 0.21 |
| I-9 | 1.0 | 11.8 | 0.23 |
| I-10 | 0.5 | 12.1 | 0.28 |
| I-11 | 0.0 | 19.3 | 0.66 |
| I-12 | -0.5 | 17.0 | 0.03 |
| I-13 | -1.0 | 17.4 | 1.63 |
2 SD+Baseline = 6.49
DLMO = 1.61 hrs
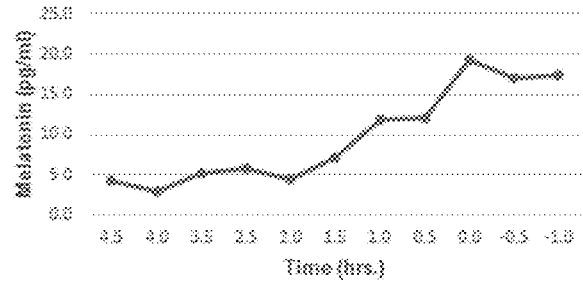
Donor I, Salimetrics
| Sam ID | Time (hrs) | Mean (pg/ml) | SD |
|---|---|---|---|
| I-2 | 4.5 | 6.4 | 1.89 |
| I-3 | 4.0 | 9.5 | 1.98 |
| I-4 | 3.5 | 6.1 | 0.45 |
| I-6 | 2.5 | 3.8 | 0.12 |
| I-7 | 2.0 | 6.4 | 0.10 |
| I-8 | 1.5 | 16.5 | 1.70 |
| I-9 | 1.0 | 18.7 | 5.02 |
| I-10 | 0.5 | 48.5 | 2.07 |
| I-11 | 0.0 | 50.0 | 0.00 |
| I-12 | -0.5 | 50.0 | 0.00 |
| I-13 | -1.0 | 50.0 | 0.00 |
2 SD+Baseline = 11.13
DLMO = 1.77 hrs
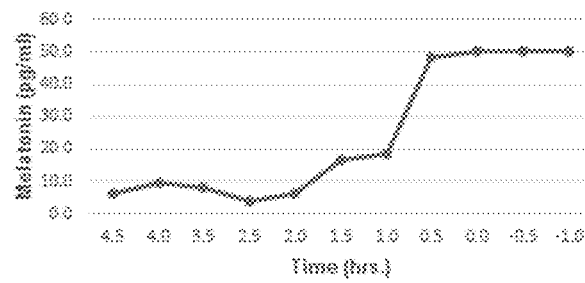
Donor I, Buhlmann
| Sam ID | Time (hrs) | Normalized Salimetrics | Normalized Buhlmann |
|---|---|---|---|
| I-2 | 4.0 | 0.44 | 0.26 |
| I-3 | 3.5 | 0.29 | 0.39 |
| I-4 | 3.0 | 0.53 | 0.33 |
| I-6 | 2.5 | 0.59 | 0.16 |
| I-7 | 2.0 | 0.46 | 0.26 |
| I-8 | 1.5 | 0.72 | 0.66 |
| I-9 | 1.0 | 1.21 | 0.77 |
| I-10 | 0.5 | 1.24 | 1.99 |
| I-11 | 0.0 | 1.98 | 2.05 |
| I-12 | -0.5 | 1.74 | 2.06 |
| I-13 | -1.0 | 1.78 | 2.05 |
| DLMO = | | 0.67 | 0.46 |
(Red shading shows approximate DLMO time before final calculation)
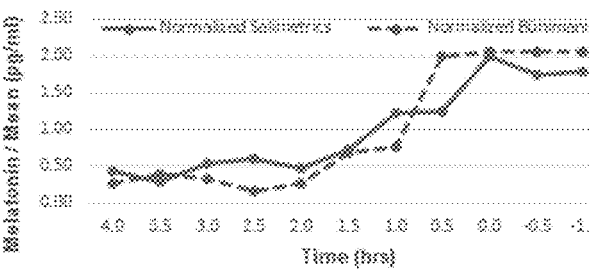
Donor I, Normalized

FIGURE 4E
| Sam ID | Time (hrs) | Mean (pg/ml) | SD |
|---|---|---|---|
| J-1 | 5.0 | 0.9 | 0.45 |
| J-2 | 4.5 | 0.0 | 0.00 |
| J-3 | 4.0 | 0.0 | 0.00 |
| J-4 | 3.5 | 1.6 | 0.26 |
| J-5 | 3.0 | 3.6 | 0.09 |
| J-6 | 2.5 | 2.9 | 1.40 |
| J-7 | 2.0 | 6.3 | 0.51 |
| J-8 | 1.5 | 5.6 | 0.04 |
| J-9 | 1.0 | 6.4 | 0.32 |
| J-10 | 0.5 | 6.0 | 0.01 |
| J-11 | 0.0 | 8.2 | 0.74 |
| J-12 | -0.5 | 7.9 | 0.60 |
| J-13 | -1.0 | 8.8 | 0.35 |
2 SD+Baseline = 1.36
DLMO = 3.56 hrs
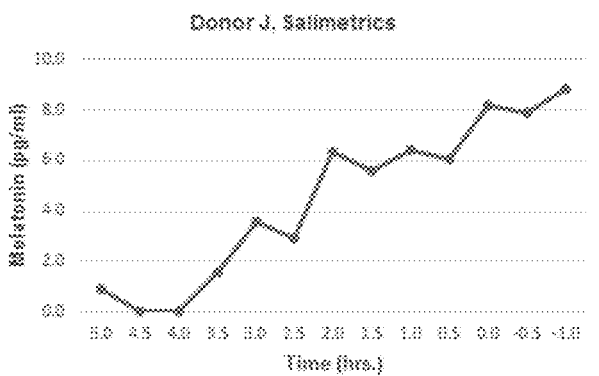
| Sam ID | Time (hrs) | Mean (pg/ml) | SD |
|---|---|---|---|
| J-1 | 5.0 | 2.1 | 0.64 |
| J-2 | 4.5 | 1.6 | 0.21 |
| J-3 | 4.0 | 3.0 | 1.66 |
| J-4 | 3.5 | 5.1 | 0.22 |
| J-5 | 3.0 | 8.9 | 0.37 |
| J-6 | 2.5 | 10.4 | 0.26 |
| J-7 | 2.0 | 13.4 | 1.64 |
| J-8 | 1.5 | 14.2 | 0.73 |
| J-9 | 1.0 | 18.2 | 0.68 |
| J-10 | 0.5 | 18.2 | 2.81 |
| J-11 | 0.0 | 41.5 | 11.98 |
| J-12 | -0.5 | 29.4 | 3.84 |
| J-13 | -1.0 | 24.7 | 2.38 |
2 SD+Baseline = 3.60
DLMO = 3.85 hrs
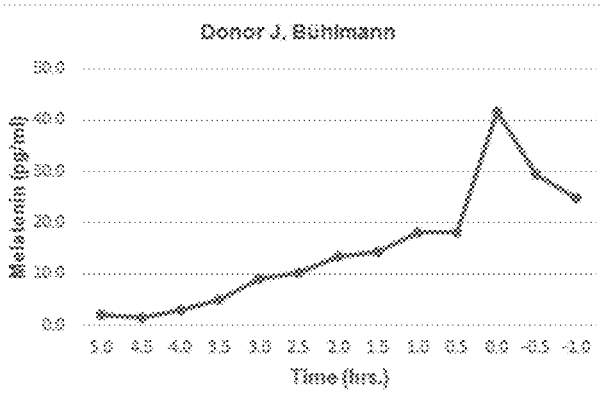
| Donor ID | Time (hrs) | Normalized Salimetrics | Normalized Bühlmann |
|---|---|---|---|
| J-1 | 5.0 | 0.20 | 0.14 |
| J-2 | 4.5 | 0.00 | 0.11 |
| J-3 | 4.0 | 0.00 | 0.20 |
| J-4 | 3.5 | 0.34 | 0.35 |
| J-5 | 3.0 | 0.80 | 0.61 |
| J-6 | 2.5 | 0.65 | 0.71 |
| J-7 | 2.0 | 1.42 | 0.91 |
| J-8 | 1.5 | 1.25 | 0.97 |
| J-9 | 1.0 | 1.43 | 1.24 |
| J-10 | 0.5 | 1.35 | 1.24 |
| J-11 | 0.0 | 1.83 | 2.83 |
| J-12 | -0.5 | 1.76 | 2.00 |
| J-13 | -1.0 | 1.97 | 1.68 |
DLMO = 0.30   0.26
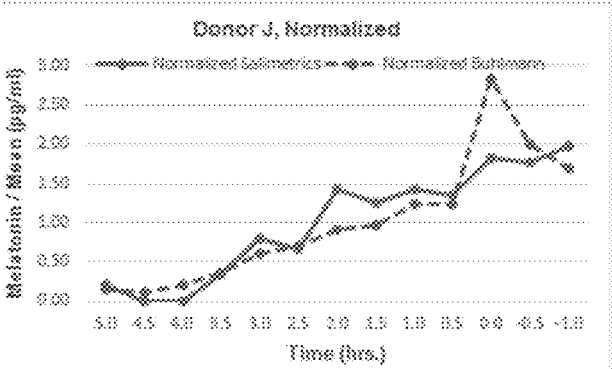
(Red shading shows approximate DLMO time before final calculation)

| Sample Mixtures | | Observed pg/ml | Expected pg/ml | Recovery (%) |
|---|---|---|---|---|
| Low | High | | | |
| 100% | 0% | 5.6 | 5.6 | NA |
| 90% | 10% | 7.9 | 9.1 | 86 |
| 80% | 20% | 11.5 | 12.6 | 91 |
| 70% | 30% | 13.6 | 16.2 | 84 |
| 60% | 40% | 19.5 | 19.7 | 99 |
| 50% | 50% | 22.4 | 23.2 | 96 |
| 40% | 60% | 26.2 | 26.8 | 98 |
| 30% | 70% | 32.0 | 30.3 | 105 |
| 20% | 80% | 33.2 | 33.9 | 98 |
| 10% | 90% | 37.1 | 37.4 | 99 |
| 0% | 100% | 40.9 | 40.9 | NA |
| | | | Average | 95 |

…

MELATONIN MONOCLONAL ANTIBODY, DETECTION, METHODS AND USES THEREOF

RELATED APPLICATIONS

This application is the National Phase of International Application No. PCT/US2014/029257, filed Mar. 14, 2014, which designated the U.S. and that International Application was published under PCT Article 21(2) in English, which claims priority to U.S. Provisional Application No. 61/809,751, filed Apr. 8, 2013, and U.S. Provisional Application No. 61/794,713, filed Mar. 15, 2013, all of which applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Sep. 11, 2015, is named "SALIMETRICSO443173.TXT" and is 9,995 bytes in size.

INTRODUCTION

Melatonin (N-acetyl-5-methoxytryptamine) is a hormone that originates in the pineal gland, but is also synthesized in many other tissues and cells. Melatonin exerts a wide range of effects throughout the body. It plays a role in regulating the circadian rhythm and also functions as a biological response modifier for a wide range of physiological conditions, such as hormone and immune regulation.

In humans, nocturnally peaking oscillations of melatonin are involved in sleep-wakefulness where melatonin concentrations are lower during the day [1,2]. In recent years, the role of melatonin and its metabolites have been identified as potent, broad acting antioxidants and free radical scavengers in addition to playing a role in the upregulation of antioxidant enzymes [reviewed in 3,4].

Melatonin levels are typically measured in plasma. The current commercially available melatonin ELISAs rely upon either polyclonal antibodies (pAbs) or Mouse monoclonal antibodies (mAbs), which require complex, overnight incubations (18 to 22 hours) to attain satisfactory performance characteristics (Kennaway et al., Endocrinology 1982, 110 (5) 1766-1772; Blair et al., Aust J Chem 1979, (32) 399-403). In addition, these conventional assays employing polyclonal Abs to melatonin often require an extraction step which becomes cumbersome when many samples are handled and contributes to an increase in assay variation. Mouse monoclonal antibodies on the other hand may not achieve the level of sensitivity required for detecting low levels of a compound such as melatonin. Therefore, there is a need for alternative reagents, and methods and uses for melatonin detection.

Rabbits are a suitable host for developing antibodies against low immunogenic material due to the more diverse immune response compared to rodents. The extensive gene conversion and somatic hypermutation during a longer affinity maturation process, as well as a more diverse light chain repertoire, all contributes to the higher diversity of antibody response in rabbits. The rabbit's unique immune system and large number of splenocytes allows the generation of larger numbers of antibodies targeting more diverse epitopes (Knight et al., Advances in Immunology 56: pp. 179-218, 1994; Schiaffella et al., J Immunol 162: pp. 3,984-3,995, 1999).

SUMMARY

Measurement of salivary melatonin is advantageous, especially to avoid invasive venipuncture procedures. The invention provides compositions, methods and uses for determining, detecting, measuring, screening for, analyzing and monitoring melatonin.

Accordingly, monoclonal antibodies and fragments thereof that specifically bind to melatonin are provided. In one embodiment, an antibody or fragment thereof includes: a heavy chain variable region comprising a CDR-H1 sequence comprising at least 80% (or more) sequence identity with the sequence of SEQ ID NO: 7, a CDR-H2 sequence comprising at least 90% (or more) sequence identity with the sequence of SEQ ID NO: 8, and a CDR-H3 sequence comprising at least 80% (or more) sequence identity with the sequence of SEQ ID NO: 9; and/or a light chain variable region comprising a CDR-L1 sequence comprising at least 80% (or more) sequence identity with the sequence of SEQ ID NO: 17, a CDR-L2 sequence comprising at least 80% (or more) sequence identity with the sequence of SEQ ID NO: 18, and a CDR-L3 sequence comprising at least 80% (or more) sequence identity with the sequence of SEQ ID NO: 19.

In various additional embodiments, an antibody or fragment thereof includes: a heavy chain variable region ($V_H$) and/or light chain variable region ($V_L$) with a CDR with at least 85%, 86%, 87%, 88%, 89%, 90%, or more identity to a reference heavy chain variable region (VH) and/or a reference and/or light chain variable region (VL), e.g., any of SEQ ID NOs: 6-9 or 16-19. In further additional embodiments, an antibody or fragment thereof includes: a heavy chain variable region ($V_H$) and/or light chain variable region ($V_L$) with a CDR with at least 90%, 91%, 92%, 93%, 94%, 95%, or more identity to a reference heavy chain variable region (VH) and/or a reference and/or light chain variable region (VL), e.g., any of SEQ ID NOs: 6-9 or 16-19. In yet additional embodiments, an antibody or fragment thereof includes: a heavy chain variable region ($V_H$) and/or light chain variable region ($V_L$) with a CDR with at least 95%, 96%, 97%, 98%, 99%, or 100% identity to a reference heavy chain variable region (VH) and/or a reference and/or light chain variable region (VL), any of e.g., SEQ ID NOs: 6-9 or 16-19.

Antibodies and fragments thereof can also include a heavy chain constant region ($C_H$) and/or a light chain constant region ($C_L$). In various embodiments, an antibody or fragment thereof includes a heavy chain constant region ($C_H$) having at least 80% sequence identity to a reference sequence, e.g., SEQ ID NO: 10; and/or a light chain constant region ($C_L$) having at least 80% sequence identity to a reference sequence, e.g., SEQ ID NO: 20. In additional embodiments, a heavy chain constant region ($C_H$) has at least 85% sequence identity to reference sequence, e.g., SEQ ID NO: 10; or a light chain constant region ($C_L$) having at least 85% sequence identity to a reference sequence, e.g., SEQ ID NO: 20. Additional embodiments include sequences with 90% or greater (91%, 92%, 93%, 94%, 95%, 96%, 97%, 98%, 99%, or 100%) identity to a reference sequence, e.g., a heavy chain constant region ($C_H$) with the sequence of SEQ ID NO: 10; and/r a light chain constant region ($C_L$) with the sequence of SEQ ID NO: 20.

Antibodies and fragments thereof also include a heavy chain variable region ($V_H$) and/or light chain variable region ($V_L$) and/or a heavy chain constant region ($C_H$) and/or a light chain constant region ($C_L$) with one or more (a plurality of) modifications, e.g., any of SEQ ID NOs:1-20. In one embodiment, an antibody or fragment thereof has 1-2, 2-3, 3-4, 5-6, 6-7, 7-8, 8-9, 9-10, 10-15, 15-20, 20-25, 25-30 amino acid substitutions, deletions or insertions of a heavy chain variable region ($V_H$) and/or light chain variable region ($V_L$) and/or a heavy chain constant region ($C_H$) and/or a light chain constant region ($C_L$), within or outside the heavy or the light chain variable region sequence (e.g., within or outside a complementarity determining region (CDR) and/or a framework region (FR) of the heavy or the light chain variable region sequence), within or outside the heavy chain constant region ($C_H$) or a light chain constant region ($C_L$). Thus, substitutions, deletions and insertions can be but need not be within one or more CDRs, e.g., one or more CDRs do not have an amino acid substitution, deletion or insertion. Substitutions include conservative and non-conservative amino acid substitutions.

Antibody fragments thereof of heavy chain variable region ($V_H$) and/or light chain variable region ($V_L$) and/or heavy chain constant region ($C_H$) and/or light chain constant region ($C_L$) can be of various lengths, but typically are least one amino acid residue in length less than a full length antibody. In particular embodiments, a fragment length is from about 50 to 100 amino acids in length. Exemplary fragments include an Fab, Fab', F(ab')$_2$, Fv, Fd, single-chain Fv (scFv), disulfide-linked Fvs (sdFv), $V_L$, $V_H$, diabody (($V_L$-$V_H$)$_2$ or ($V_H$-$V_L$)$_2$), triabody (trivalent), tetrabody (tetravalent), minibody ((scF$_V$-C$_H$3)$_2$), IgGdeltaCH2, scFv-Fc or (scFv)$_2$-Fc fragment.

Antibodies and fragments thereof also include mammalian antibodies. Exemplary mammalian antibodies include, for example, rabbit monoclonal antibodies, human monoclonal antibodies and humanized monoclonal antibodies. Antibodies and fragments thereof can be of any isotype, such as an IgG, IgA, IgE, IgM or IgD isotype.

Antibodies and fragments thereof have binding affinity for melatonin. In various embodiments, an antibody or fragment thereof or the VH or VL has a binding affinity ($K_d$) for binding to melatonin from about $10^{-5}$M to about $10^{-13}$M. In various additional embodiments, an antibody or fragment thereof specifically binds to melatonin with sensitivity to melatonin concentrations of less than or equal to about 1 pg/ml.

In further embodiments, an antibody or fragment thereof specifically binds to melatonin with about the same, similar, or greater affinity constant (stronger binding) than does the monoclonal antibody or fragment thereof or the VH or VL including a reference heavy chain variable region (VH) and/or a reference and/or light chain variable region (VL), any of e.g., SEQ ID NOs:6-9 or 16-19, for binding to melatonin. In particular aspects, a monoclonal antibody or fragment thereof or the VH or VL as set forth herein exhibits negligible binding to (is not sensitive to) N-acetyl-5-hydroxy-tryptamine, 5-methoxy-tryptamine, 6-hydroxy-melatonin, and/or L-tryptophan.

The invention further provides nucleic acid sequences that encode antibodies and fragments thereof. In various embodiments, a nucleic acid coding for a heavy chain variable region ($V_H$) of an antibody has at least 80% (or greater) sequence identity with the sequence of SEQ ID NO: 1; and/or coding for a light chain variable region (VL) that has at least 80% (or greater) sequence identity with the sequence of SEQ ID NO: 11. In various additional embodiments, a nucleic acid coding for a heavy or light chain constant region of an antibody has at least 80% (or greater) sequence identity with the sequence of SEQ ID NO: 5; and/or at least 80% sequence identity (or greater) with the sequence of SEQ ID NO: 15. Vectors including expression vectors that include a nucleic acid encoding antibodies and fragments thereof such as a heavy or light chain variable region of an antibody has at least 80% (or greater) sequence identity with the sequence of SEQ ID NO: 1; and/or has at least 80% (or greater) sequence identity with the sequence of SEQ ID NO: 11.

The invention additionally provides a monoclonal antibody- or fragment thereof-melatonin complex. In one embodiment, a monoclonal antibody- or fragment thereof-melatonin complex includes a monoclonal antibody or fragment thereof or a VH or VL chain as set forth herein bound to melatonin.

The invention moreover provides monoclonal antibody- or fragment thereof-solid support and/or a solid phase complex. In one embodiment, a monoclonal antibody- or fragment thereof-solid support and/or a solid phase complex includes a monoclonal antibody or fragment thereof or a VH or VL chain as set forth herein, and a solid support and/or a solid phase linked thereto.

Invention monoclonal antibody-melatonin-solid support and/or a solid phase complex include, in various aspects, a monoclonal antibody or fragment thereof or a VH or VL chain as set forth herein bound to melatonin. For example, in a non-limiting aspect, the solid support and/or a solid phase is linked to the monoclonal antibody or fragment thereof or the VH or VL chain.

The invention still further provides a conjugate that includes a monoclonal antibody or fragment thereof or a VH or VL chain as set forth herein, and a detectable moiety. For example, in a non-limiting aspect, the monoclonal antibody or fragment thereof or a VH or VL chain as set forth herein is linked to the detectable moiety.

Monoclonal antibodies, fragments thereof or VH or VL chains as set forth herein, as well as complexes and conjugates include isolated and/or purified forms. Monoclonal antibodies, fragments thereof or VH or VL chains as set forth herein may also be included in compositions. In particular aspects, compositions include, for example a sterile composition and/or a pharmaceutical composition.

Host cells that produce monoclonal antibodies, fragments thereof and VH or VL chains as set forth herein, are also provided.

Methods for producing monoclonal antibodies, fragments thereof and VH or VL chains as set forth herein, are also provided. In one embodiment, a method includes culturing in suitable medium and culture conditions a host cell expressing an antibody heavy chain variable region ($V_H$) with at least 80% (or more) sequence identity to the amino acid sequence SEQ ID NO: 6 and/or an antibody light chain variable region ($V_L$) with at least 80% (or more) sequence identity to the sequence SEQ ID NO: 16, so that antibodies, fragments thereof or VH or VL chains as set forth herein are produced; and recovering the produced antibodies, fragments thereof or VH or VL chains as set forth herein from the culture medium and/or from the host cells.

The invention yet also provides melatonin-detectable moiety conjugates. In one embodiment, a melatonin-detectable moiety conjugate includes a melatonin molecule having a nitrogen at the indole N1 position and a detectable moiety. In a particular aspect, an optional linker links the melatonin nitrogen at the indole N1 position to the detectable moiety. Non-limiting exemplary detectable moieties include horse radish peroxidase (HRP), alkaline phosphatase, glucose oxidase, glucose-6-phosphate dehydrogenase, malate dehydrogenase, staphylococcal nuclease, delta-V-steroid isomerase, yeast alcohol dehydrogenase, alpha-glycerophosphate, dehydrogenase, triose phosphate isomerase, asparaginase, beta-galactosidase, ribonuclease, urease, catalase, glucoamylase, acetylcholinesterase, biotin, iminobiotin, a fluorophore, a fluorescent protein, chromophore, chemiluminescent material, phosphorescent material, an electrochemiluminescent tag, a radionucleotide, and combinations thereof.

The invention yet additionally provides a melatonin-carrier compound. In one embodiment, a melatonin-carrier compound includes a melatonin molecule having a nitrogen at the indole N1 position, and a carrier molecule linked thereto. In a particular aspect, an optional linker links the melatonin, for example, at the indole N1 position to the carrier compound/molecule.

The invention yet further provides a method for determining an amount of melatonin in a sample (e.g., a biological sample). In one embodiment, a method includes contacting a melatonin binding monoclonal antibody or fragment thereof (or the VH or VL set forth herein) to a sample, under conditions wherein any melatonin in the sample binds to the monoclonal antibody or fragment, and contacting the melatonin binding monoclonal antibody or fragment with the melatonin-detectable moiety conjugate under conditions where the melatonin-detectable moiety conjugate binds to the monoclonal antibody or fragment, such that any melatonin in the sample competes with the melatonin-detectable moiety conjugate for binding to the antibody or fragment. Subsequently, removing the melatonin-detectable moiety conjugate not bound to the monoclonal antibody or fragment, and determining the amount of detectable moiety conjugate present, where the amount of melatonin in the sample is inversely proportional to the amount of detectable moiety conjugate present, thereby determining the amount of melatonin in a sample. In another embodiment, a method includes contacting a sample with a monoclonal antibody or fragment thereof or a VH or VL set forth herein, under conditions where the monoclonal antibody, fragment, VH or VL binds to any melatonin in the sample. Subsequently the amount of melatonin in the sample is determined.

Additional compositions and method steps may be incorporated. Non-limiting examples include: a diluent solution to dilute the biological sample, such as tris buffered saline (TBS) or phosphate buffered saline (PBS); linking the monoclonal antibody, fragment thereof or the VH or VL chain to a support and/or a solid phase, such as an inert material; performing the assay on substrate, such as a multi-well plate or dish, performing the assay in a point of care environment or as a device.

Various optional features of the invention methods and uses also include completing determining, detecting, measuring, screening for, analyzing or monitoring melatonin within 12 hours or less, 10 hours or less, 8 hours or less, 6 hours or less or 4 hours or less (e.g., about 3 hours).

DESCRIPTION OF THE DRAWINGS

FIG. 2 shows exemplary variable heavy chain (VH) and variable light chain (VL) of exemplary Melatonin binding antibody. CDRs are indicated by CDR1, CDR2 and CDR3 over the bold/underlined sequence region. The variable heavy chain (VH) and variable light chain (VL) of exemplary Melatonin antibody, and corresponding CDRs are also identified by sequence identifiers (SEQ ID NOs:1-20)

FIGS. 4A-4E show plots of saliva melatonin levels of five Donors (A-E) over time as determined by two different assays, and a normalized (overlay) plot.

DETAILED DESCRIPTION

Figure 1:
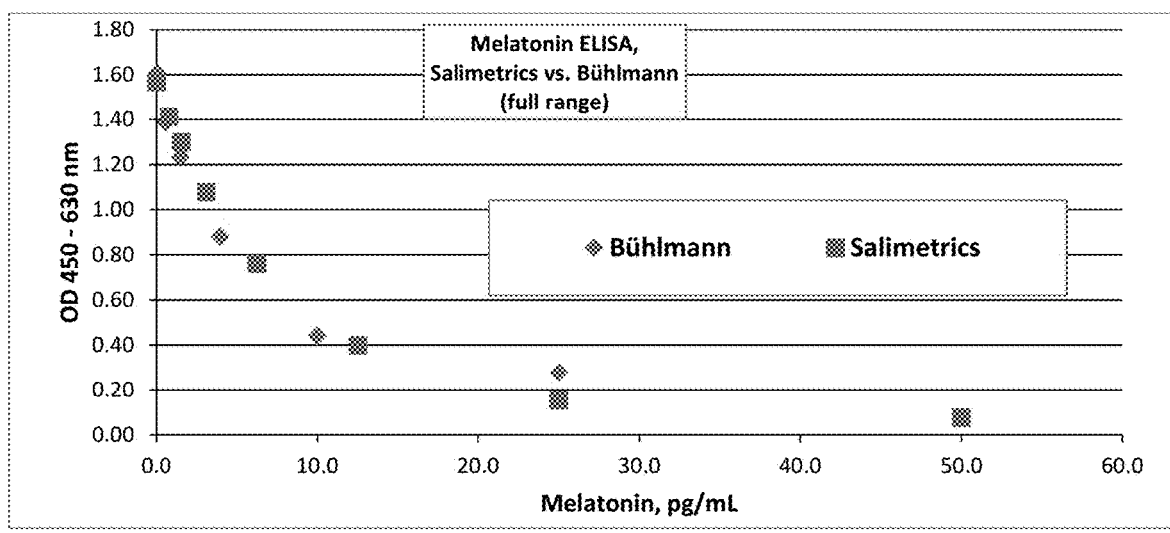
FIG. 1 shows a plot of a melatonin enzyme-linked immunosorbent assay (ELISA) comparison.

In accordance with the invention there are provided monoclonal antibodies and fragments thereof that bind to melatonin, and VH and VL chains of monoclonal antibody. In various embodiments, there are provided compositions and methods for producing a monoclonal antibody that binds to melatonin using a unique linkage for melatonin immunization. In additional embodiments, there are provided methods and uses of monoclonal antibody, and fragments thereof that bind to melatonin, and VH and VL chains of monoclonal antibody, for determining, detecting, measuring, screening for, analyzing and monitoring melatonin. In further embodiments, there is provided melatonin conjugated to a detectable label (reporter group) and methods and uses of melatonin conjugated to a detectable label (reporter group) for a rapid and sensitive ELISA assay for determining, detecting, measuring, screening for, analyzing and monitoring melatonin.

A "protein," a "polypeptide," or a "peptide" sequence is a chain of amino acids or "residues" in a particular order or sequence. Residues of amino acid sequences can be linked by natural amide bonds, or by non-natural or non-amide chemical bonds. Non-natural and non-amide chemical bonds include, for example, those formed with glutaraldehyde, N-hydroxysuccinimide esters, bifunctional maleimides, or N, N'-dicyclohexylcarbodiimide (DCC).

An "antibody" refers to a polypeptide or protein that binds to other molecules (antigens) via heavy and/or light chain variable domains, $V_H$ and/or $V_L$, respectively. An "antibody" refers to any monoclonal or polyclonal immunoglobulin molecule of any isotype, such as IgG, IgA, IgD, IgE, IgM, and any subclass thereof (e.g., $IgG_1$, $IgG_2$, $IgG_3$ or $IgG_4$). Antibodies include full-length antibodies that include two heavy and two light chain sequences. The terms "antibody", "monoclonal antibody", and combinations or variants of these are considered to include antigen-binding fragments (subsequences) of such an antibody, immunoreactive (target binding) fragments of such an antibody, and antigen-binding derivatives of such an antibody, such as antigen-binding derivatives including one or more (e.g., all) of the complementary determining regions (CDR), unless otherwise stated or clear from the context.

An antibody that includes or consists of a $V_H$ chain and/or $V_L$ chain or fragment of a $V_H$ chain and/or $V_L$ chain can include a single $V_H$ chain or $V_L$ chain or a single $V_H$ chain or $V_L$ chain fragment, or a plurality (2, 3, 4 or more) of $V_H$ chains and/or $V_L$ chains, or a plurality of fragments of $V_H$ chains and/or $V_L$ chains. An antibody or fragment thereof may be an oligomeric (higher order or valent) forms, such as a trimer, tetramer, pentamer, hexamer, heptamer, and so forth, or fragments thereof, or $V_H$ chain, $V_L$ chain.

A "monoclonal antibody" as used herein can include an antibody that is part of a substantially homogeneous population of antibodies that are obtained from or derived from a single clone, including any eukaryotic, prokaryotic, or phage clone such as a single B lymphocyte clone. A "monoclonal" antibody is therefore defined structurally, and not by the method by which it is produced.

Antibodies and fragments thereof include mammalian, rabbit, primatized, humanized and fully human antibodies and fragments thereof. Antibodies and fragments thereof include those produced or expressed by or on host cells or hybridomas, or B cells, or those produced synthetically or by other organisms (plant, insect, bacteria, etc.).

A mammalian antibody is an antibody produced by a mammal, transgenic or non-transgenic, or a non-mammalian organism engineered to produce a mammalian antibody. For example, a non-mammalian cell (bacteria, yeast, insect cell), animal or plant can be engineered to produce a mammalian antibody.

A "rabbit" antibody means that the amino acid sequence of the antibody is fully rabbit. Thus, all of the amino acids are rabbit or exist in a rabbit antibody.

A "human" antibody means that the amino acid sequence of the antibody is fully human, i.e., human heavy and human light chain variable and human constant regions. Thus, all of the amino acids are human or exist in a human antibody.

A "humanized" antibody, means that the amino acid sequence of the antibody has non-human amino acid residues (e.g., rabbit, mouse, rat, goat, etc.) of one or more complementarity determining regions (CDRs) that specifically bind to a desired antigen in an acceptor human immunoglobulin molecule, and one or more human amino acid residues in the Fv framework region (FR), which are amino acid residues that flank the CDRs. Thus, by way of example one or more rabbit antibody $V_H$ or $V_L$ chain CDRs as disclosed herein in a human acceptor acceptor human immunoglobulin molecule.

Antibodies include fragments (subsequences). Non-limiting representative antibody fragments (subsequences) include but are not limited to Fab, Fab', F(ab')$_2$, Fv, Fd, single-chain Fv (scFv), disulfide-linked Fvs (sdFv), $V_L$, $V_H$, Camel Ig, V-NAR, VHH, trispecific (Fab$_3$), bispecific (Fab$_2$), diabody (($V_L$-$V_H$)$_2$ or ($V_H$-$V_L$)$_2$), triabody (trivalent), tetrabody (tetravalent), minibody ((scF$_V$-$C_H$3)$_2$), bispecific single-chain Fv (Bis-scFv), IgGdeltaCH2, scFv-Fc, (scFv)$_2$-Fc, affibody, aptamer, avimer or nanobody, or other antigen (e.g., melatonin) binding fragments of an intact immunoglobulin. Antibodies include those that bind to more than one epitope (e.g., bi-specific antibodies), or antibodies that can bind to one or more different antigens (e.g., bi- or multi-specific antibodies).

Invention antibodies, fragments thereof, or $V_H$ chain, $V_L$ chain of an antibody include those with sequence identity to a reference an antibody, fragment, or $V_H$ chain, $V_L$ chain of an antibody set forth herein (e.g., SEQ ID NOs:1-20). For example, a sequence that has at least 65%, 70%, 75%, 80%, 85%, 90%, 95%, 96%, 97%, 98%, 99%, 99.5%, or 99.8% sequence identity with the exemplified sequences set forth herein (e.g., SEQ ID NOs:1-20) are included in the invention. Accordingly, a heavy and or light chain variable region of an amino acid sequence of an antibody may vary from the sequences set forth herein and still be within the scope of embodiments disclosed herein. For example, one or more complementarity determining regions (CDRs) may be different from those of a heavy and or light chain variable region of an amino acid sequence of an antibody as set forth herein (e.g., SEQ ID NOs:7-9 and/or 17-19). Alternatively, one or more complementarity determining regions (CDRs) may be identical to the sequences set forth herein (e.g., SEQ ID NOs:7-9 and/or 17-19), but other portions of the heavy or light chain variable region may vary. Such sequence variations of the exemplified sequences set forth herein (e.g., SEQ ID NOs:1-20) are to be considered as embodiments within the scope of the invention disclosed herein.

The term "identity" and grammatical variations thereof, mean that two or more referenced entities are the same. Thus, where two sequences are identical, they have the same sequence, at least within the referenced region or portion. The identity can be over a defined area (region or domain) of the sequence. An "area" or "region of identity" refers to a portion of two or more referenced entities that are the same. Thus, where two sequences are identical over one or more sequence regions they share identity within that region.

The "percent (%) amino acid sequence identity" with respect to an amino acid (i.e., peptide or polypeptide) sequence can be defined as the percentage of amino acid residues in a candidate sequence that are identical with the amino acid residues in the amino acid sequence to which comparison is made, after aligning the sequences and introducing gaps, if necessary, to achieve the maximum percent sequence identity, and, optionally, not considering conservative substitutions as part of the sequence identity.

The percent identity can extend over the entire sequence length of the sequence. In particular aspects, the length of the sequence region sharing the percent identity is 5 or more contiguous amino acids, e.g., 5, 6, 7, 8, 9, 10, 11, 12, 13, 14, 15, 16, 17, 18, 19, 20, 21, 22, 23, 24, 25, etc. contiguous amino acids. In additional particular aspects, the length of the sequence sharing the percent identity is 25 or more contiguous amino acids, e.g., 26, 27, 28, 29, 30, 31, 32, 33, 34, 35, etc. contiguous amino acids. In further particular aspects, the length of the sequence sharing the percent identity is 35 or more contiguous amino acids, e.g., 35, 36, 37, 38, 39, 40, 41, 42, 43, 44, 45, 45, 47, 48, 49, 50, etc., contiguous amino acids. In yet additional particular aspects, the length of the sequence sharing the percent identity is 50 or more contiguous amino acids, e.g., 50-55, 55-60, 60-65, 65-70, 70-75, 75-80, 80-85, 85-90, 90-95, 95-100, 100-110, etc. contiguous amino acids.

The terms "homologous" or "homology" mean that two or more referenced entities share at least partial identity over a given region or portion. "Areas, regions or domains" of homology or identity mean that a portion of two or more referenced entities share homology or are the same. Thus, where two sequences are identical over one or more sequence regions they share identity in these regions. "Substantial homology" means that a molecule is structurally or functionally conserved such that it has or is predicted to have at least partial structure or function of one or more of the structures or functions (e.g., a biological function or activity) of the reference molecule, or relevant/corresponding region or portion of the reference molecule to which it shares homology.

The extent of identity (homology) between two sequences can be ascertained using a computer program and mathematical algorithm known in the art. Such algorithms that calculate percent sequence identity (homology) generally account for sequence gaps and mismatches over the comparison region or area. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate extent of identity (Pearson et al., *Proc. Natl. Acad. Sci.* USA 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

An antibody, fragment thereof, or VH or VL chain (or CDR) of an antibody with substantial homology to a reference sequence as set forth herein (e.g., SEQ ID NOs:1-20) has or is predicted to have at least partial activity or function as the reference sequence. Accordingly, antibodies, fragments thereof, and VH or VL chain (or CDR) of an antibody include those that have at least a part of an "activity" or "function" as a reference antibody, fragment, or VH or VL chain of an antibody (e.g., SEQ ID NOs:1-20), for example, binding affinity (e.g., $K_d$), or binding specificity.

The term "at least a part" means that the antibody, fragment thereof, or VH or VL chain of an antibody may have less activity or function but the antibody, fragment thereof, or VH or VL chain of an antibody retains at least a measurable or detectable amount of the activity or function of the reference antibody, fragment thereof, or VH or VL chain of an antibody exemplified herein (e.g., SEQ ID NOs:1-20), but may also have a greater activity or function than a reference antibody, fragment thereof, or VH or VL chain of an antibody exemplified herein (e.g., SEQ ID NOs:1-20).

Invention antibodies, fragments thereof, or $V_H$ chain, $V_L$ chain of an antibody also include those that compete for binding to a target. Thus, for example, a given antibody, fragment, or $V_H$ chain, $V_L$ chain of an antibody may inhibit or compete for binding of another antibody, fragment, or $V_H$ chain, $V_L$ chain of an antibody for binding to melatonin. In a particular non-limiting example, an antibody, fragment, or $V_H$ chain, $V_L$ chain of an antibody may inhibit binding by at least 30%, at least 35%, at least 40%, at least 45%, at least 50%, at least 55%, at least 60%, at least 65%, at least 70%, at least 75%, at least 80%, at least 85%, at least 90%, or at least 95%, or more of any reference antibody, fragment, or $V_H$ chain, $V_L$ chain of an antibody set forth herein for binding to melatonin. Accordingly, antibodies, fragments, $V_H$ and $V_L$ chains of an antibody include those that compete with any of the sequences (SEQ ID NOs:1-20) as set forth herein for binding to melatonin.

Invention antibodies, fragments thereof, or $V_H$ chain, $V_L$ chain of an antibody further include those having more or less affinity for target (e.g., melatonin) than a reference antibody, fragment, or $V_H$ chain, $V_L$ chain of an antibody. For example, an antibody, fragment, or $V_H$ chain, $V_L$ chain of an antibody can have more or less affinity melatonin and include a sequence at least 60% or more (e.g., 65%, 70%, 75%, 80%, 85%, 90%, 95%, 96%, 97%, 98%, 99%, etc.) identical to an antibody, fragment, or $V_H$ chain, $V_L$ chain of an antibody sequence set forth as SEQ ID NOs:1-20, or sequence at least 60% or more (e.g., 65%, 70%, 75%, 80%, 85%, 90%, 95%, 96%, 97%, 98%, 99%, etc.) identical to a $V_H$ chain or $V_L$ chain of an antibody sequence set forth as SEQ ID NOs:6 or 18.

Invention antibodies, fragments thereof, or $V_H$ chain, $V_L$ chain of an antibody therefore include those having the same or different binding affinity for melatonin. For example, an antibody, fragment, or $V_H$ chain, $V_L$ chain of an antibody may have an affinity for target (e.g., melatonin) that is greater or less than 2-5, 5-10, 10-100, 100-1000 or 1000-10,000 fold affinity or any numerical value or range or value within such ranges, as another antibody, fragment, or $V_H$ chain, $V_L$ chain of an antibody, for example, any of SEQ ID NOs:1-20. Exemplary binding affinities of an antibody, fragment, or $V_H$ chain, $V_L$ chain of an antibody for a target (e.g., melatonin) have a dissociation constant ($K_d$) less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M. Typically, binding affinities ($K_d$) for target (e.g., melatonin) will be less than $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, or $10^{-12}$ M.

"Sensitivity" to a particular concentration of a compound, such as melatonin, as used herein can mean that the compound can be detected at that particular or a greater concentration. For example, an antibody, fragment, or $V_H$ chain, $V_L$ chain of an antibody can detect melatonin with a sensitivity to melatonin concentrations of about 1000, 500, 100, 80, 50, 40, 30, 20, 10, 5, 2, 1, 0.7, 0.5, 0.2, 0.1, 0.05, 0.02, or 0.01 pg/ml or greater. In a more particular aspect, a monoclonal antibody as set forth herein can detect melatonin with a sensitivity to melatonin concentrations of about 1.0 pg/ml.

As set forth herein, antibodies, fragments thereof, or VH or VL chains of antibodies can be modified. Modifications, including substitutions additions/insertions and deletions may be in the constant or variable (e.g., hypervariable, such as CDR or FR) region. One or a few amino acid substitutions in constant or variable regions are likely to be tolerated. Non-conservative substitution of multiple amino acids in hypervariable regions is likely to affect binding affinity or specificity of an antibody, fragment thereof, or VH or VL chain of an antibody. Thus, modifications include substituting, inserting, adding or deleting small and large regions of amino acid sequences of an antibody, fragment thereof, or VH or VL chain of an antibody. The modified sequence can be the same, or greater or shorter in length as the reference sequence.

Non-limiting examples of modifications include one or more amino acid substitutions (e.g., 1-3, 3-5, 5-10, 10-15, 15-20, 20-25, 25-50 or more residues), additions/insertions (e.g., 1-3, 3-5, 5-10,10-15, 15-20, 20-25, 25-50 or more residues) or deletions (e.g., subsequences or fragments) of the antibody, fragment thereof, or VH or VL chain of an antibody. In particular embodiments, a modified antibody, fragment thereof, or VH or VL chain of an antibody retains at least part of a function or an activity of a reference antibody, fragment thereof, or VH or VL chain of an antibody, e.g., binding affinity (e.g., $K_d$) or binding specificity to melatonin.

In additional particular embodiments, a heavy or light chain CDR (CDR1, CDR2 or CDR3) or FR will have 1-15, 1-12, 1-8, 1-5, 1-3 or fewer (e.g., 1 or 2) amino acid substitutions, deletions, insertions or additions. In a particular embodiment, a substitution within a variable region sequence is a conservative amino acid substitution, e.g., within a CDR or FR. In an additional embodiment, a substitution within a variable region sequence is not within a CDR. In another embodiment, a substitution, deletion, insertion or addition is within an FR. In an a further embodiment, a substitution, deletion, insertion or addition within a variable region sequence is not within an FR. Exemplary heavy chain and light chain CDR sequences are as set forth in SEQ ID NOs:7-9 and 17-19.

A particular example of an antibody modification is an alteration to have a different isotype or subclass, for example, by substitution of the heavy or light chain constant region. An alteration of Ig subclass can result in a change or an improvement in a function or activity.

Antibodies, fragments thereof, or VH or VL chains of antibodies include, for example, non-conservative and conservative substitutions of amino acid and/or polynucleotide sequences. In particular embodiments, a modified protein has one or a few (e.g., 1-5%, 5-10%, 10-20%) of the residues of total protein length, or 1-2, 2-3, 3-4, 5-10, 10-20, 20-30, 30-40, 40-50 residues substituted, with conservative or non-conservative substitutions or conservative and non-conservative amino acid substitutions. A "conservative substitution" denotes the replacement of an amino acid residue by another, chemically or biologically similar residue. Biologically similar means that the substitution does not destroy a biological activity or function. Structurally similar means that the amino acids have side chains with similar length, such as alanine, glycine and serine, or a similar size. Chemical similarity means that the residues have the same charge, or are both hydrophilic or hydrophobic.

Particular examples of conservative substitutions include the substitution of a hydrophobic residue such as isoleucine, valine, leucine or methionine for another, the substitution of a polar residue for another, such as the substitution of arginine for lysine, glutamic for aspartic acids, or glutamine for asparagine, and the like. A "conservative substitution" also includes the use of a substituted amino acid in place of an unsubstituted parent amino acid.

The structural determinants that contribute to antigen binding by an antibody, such as complementarity determining regions (CDR) and framework regions (FR) within hypervariable regions are known in the art. The location, structure and function of additional regions, such as D- and J-regions are also known. Antibodies, fragments thereof, or VH or VL chains of antibodies that bind to a given target (e.g., melatonin) will typically have one or more CDR and FR sequences with sufficient sequence identity to a heavy or light chain sequence that binds to melatonin so as to retain at least partial melatonin binding activity. For example, as exemplified herein one or more CDRs of VH or VL chains set forth as SEQ ID NOs:7-9 and or 17-19 will retain at least partial activity of binding to melatonin.

Regional mutability analysis can be used to predict the effect of particular substitutions in complementarity determining regions (CDR) and framework regions (FR) (Shapiro et al., *J Immunol.* 163:259 (1999)). In brief, sequence comparison indicates a hierarchy of mutability among di- and trinucleotide sequences located within Ig intronic DNA, which predicts regions that are more or less mutable. Quantitative structure-activity relationship (QSAR) can be used to identify the nature of the antibody recognition domain and, therefore, amino acids that participate in ligand binding. Predictive models based upon QSAR can in turn be used to predict the effect of substitutions (mutations). For example, the effect of mutations on the association and dissociation rate of an antibody interacting with its antigen has been used to construct quantitative predictive models for both kinetic ($K_a$ and $K_d$) constants, which can in turn be used to predict the effect of other mutations on the antibody (De Genst et al., *J Biol Chem.* 277:29897 (2002)). The skilled artisan can therefore use such analysis to predict amino acid substitutions that are likely to result in an antibody, fragment thereof, or VH or VL chain of an antibody that retains at least partial activity or function e.g., retains at least partial binding to melatonin.

Modified and variant proteins such as antibody, fragment thereof, or VH or VL chain of an antibody also include one or more D-amino acids substituted for L-amino acids (and mixtures thereof), structural and functional analogues, for example, peptidomimetics having synthetic or non-natural amino acids or amino acid analogues and derivatized forms. Modified and variant proteins further include "chemical derivatives," in which one or more amino acids has a side chain chemically altered or derivatized. Such derivatized polypeptides include, for example, amino acids in which free amino groups form amine hydrochlorides, p-toluene sulfonyl groups, carbobenzoxy groups; the free carboxy groups form salts, methyl and ethyl esters; free hydroxyl groups that form O-acyl or O-alkyl derivatives as well as naturally occurring amino acid derivatives, for example, 4-hydroxyproline, for proline, 5-hydroxylysine for lysine, homoserine for serine, ornithine for lysine etc. Also included are amino acid derivatives that can alter covalent bonding, for example, the disulfide linkage that forms between two cysteine residues that produces a cyclized polypeptide.

Additions and insertions include, for example, heterologous domains. An addition (e.g., heterologous domain) can be a covalent or non-covalent attachment of any type of molecule to a composition, such as a protein (e.g. antibody, fragment thereof, or VH or VL chain of the antibody) or other chemical entity (e.g. organic or inorganic compound). Typically additions and insertions (e.g., a heterologous domain) confer a complementary or a distinct function or activity.

Additions and insertions also include chimeric and fusion sequences, which is a protein sequence having one or more molecules not normally present in a reference native wild type sequence covalently attached to the sequence. The terms "fusion" or "chimeric" and grammatical variations thereof, when used in reference to a molecule, such as antibody, fragment thereof, or VH or VL chain of an antibody, means that a portions or part of the molecule contains a different entity distinct (heterologous) from the molecule as they do not typically exist together in nature. That is, for example, one portion of the fusion or chimera, such as antibody, fragment thereof, or VH or VL chain of an antibody includes or consists of a portion that does not exist together in nature, and is structurally distinct. Thus, a fusion or chimeric polypeptide is a molecule in which different portions of the polypeptide are of different protein origins. A particular example is a molecule, such as amino acid residues or a polypeptide sequence of another protein (e.g., heterologous domain) attached to antibody, fragment thereof, or VH or VL chain of the antibody to produce a chimera, or a chimeric polypeptide, to impart a distinct function.

The effect of a given modification can be assayed in order to confirm that modified antibodies, fragment, thereof, or VH or VL chain of an antibody retain at least a part of the binding activity or function of unmodified antibody, fragment thereof, or VH or VL chain of an antibody. For example, an amino acid substitution, insertion, addition, or deletion in a variable or hypervariable region of an antibody, fragment thereof, or VH or VL chain of an antibody as set forth herein (e.g., SEQ ID NOs:1-20) may be assayed for melatonin binding activity or binding specificity.

Additions and insertions further include labels and tags, which can be used to provide detection or that is useful for isolating the tagged entity. A detectable label or tag can be attached (e.g., linked or conjugated), for example, to an antibody, fragment thereof, or VH or VL chain of an antibody, or melatonin, or be within or comprise one or more atoms that comprise the antibody, fragment thereof, or VH or VL chain of an antibody, or melatonin.

A "detectable label" as used herein can refer to, for example, a chemical moiety that can be detected (e.g., imaged) or whose presence can be ascertained by a procedure described herein or known to the skilled artisan. Detectable labels include labels suitable for detection, measurement, analysis and/or quantitation, and include any composition detectable by enzymatic, biochemical, spectroscopic, photochemical, immunochemical, isotopic, electrical, optical, chemical or other means.

Non-limiting exemplary detectable labels include contrast agents (e.g., gadolinium; manganese; barium sulfate; an iodinated or noniodinated agent; an ionic agent or nonionic agent); electron-dense, magnetic and paramagnetic reagents, labels or agents (e.g., iron-oxide chelate); nanoparticles; an enzyme (horseradish peroxidase (HRP), urease, catalase, alkaline phosphatase, β-galactosidase, chloramphenicol transferase or acetylcholinesterase); a prosthetic group or ligand (e.g., biotin, streptavidin/biotin and avidin/biotin); a colorimetric label such as colloidal gold or colored glass or plastic (e.g., polystyrene, polypropylene, latex, etc.) beads; a fluorescent material, dye and fluorophore (e.g., allophycocyanin, umbelliferone, fluorescein, fluorescein isothiocyanate, fluorscamine, rhodamine, dichlorotriazinylamine fluorescein, dansyl chloride, texas red, phycoerythrin phycocyanin); a chemiluminescent or a bioluminescent material (e.g., imidazole, acridinium, oxalate, luminol, luciferase, luciferin, aequorin). A detectable label can also be any imaging agent that can be employed for detection, measurement, analysis, monitoring, and/or quantitation (e.g., for computed axial tomography (CAT or CT), fluoroscopy, single photon emission computed tomography (SPECT) imaging, optical imaging, positron emission tomography (PET), magnetic resonance imaging (MRI), gamma imaging).

Further non-limiting exemplary detectable labels include a radioactive material, such as a radioisotope, a metal or a metal oxide. "Radioactive material" refers to material that emits ionizing radiation, such as alpha particles, beta particles, or gamma rays. "Light" as used herein can refer to, for example, infrared, visible, or ultraviolet photons. "Light spectrum" as used herein can refer to, for example, the distribution of energies at different frequencies of light.

Radioisotopes include radionuclides emitting alpha, beta or gamma radiation. As the structure of antibodies, fragments thereof, or VH or VL chains of an antibody can include one or more of carbon, hydrogen, nitrogen, oxygen, sulfur, phosphorous, etc., radioisotopes of any of carbon, hydrogen, nitrogen, oxygen, sulfur, phosphorous, etc., can be included within a detectably labeled a antibody, fragment thereof, or VH or VL chain of an antibody. In particular embodiments, a radioisotope can be one or more of: C, N, O, H, S, Cu, Fe, Ga, Ti, Sr, Y, Tc, In, Pm, Gd, Sm, Ho, Lu, Re, At, Bi or Ac. In additional embodiments, a radioisotope can be one or more of: $^{3}H$, $^{10}B$, $^{18}F$ $^{11}C$, $^{14}C$, $^{13}N$, $^{18}O$, $^{15}O$, $^{32}P$, $P^{33}$, $^{35}S$, $^{35}Cl$, $^{45}Ti$, $^{46}Sc$, $^{47}Sc$, $^{51}Cr$, $^{52}Fe$, $^{57}Co$, $^{60}Cu$, $^{61}Cu$, $^{62}Cu$, $^{64}Cu$, $^{67}Cu$, $^{67}Ga$, $^{68}Ga$, $^{72}As$ $^{76}Br$, $^{77}Br$, $^{81m}Kr$, $^{82}Rb$, $^{85}Sr$, $^{89}Sr$, $^{86}Y$, $^{90}Y$, $^{95}Nb$, $^{94m}Tc$, $^{99m}Tc$, $^{97}Ru$, $^{103}Ru$, $^{105}Rh$, $^{109}Cd$, $^{111}In$, $^{113}Sn$, $^{113m}In$, $^{114}In$, $I^{125}$, $I^{131}$, $^{140}La$, $^{141}Ce$, $^{149}Pm$, $^{153}Gd$, $^{157}Gd$, $^{153}Sm$, $^{161}Tb$, $^{166}Dy$, $^{166}Ho$, $^{169}Er$, $^{169}Y$, $^{175}Yb$, $^{177}Lu$, $^{186}Re$, $^{188}Re$, $^{201}Tl$, $^{203}Pb$, $^{211}At$, $^{212}Bi$ or $^{225}Ac$. Additional non-limiting exemplary detectable labels include a metal or a metal oxide, such as gold, silver, copper, boron, manganese, gadolinium, iron, chromium, barium, europium, erbium, praseodynium, indium, or technetium.

As set forth herein, a tag can be linked or conjugated (e.g., covalently) to an antibody, fragment thereof, or VH or VL chain of an antibody, or melatonin. Non-limiting examples of tags include GST-, T7-, His-, myc-, HA- and FLAG-tags.

As disclosed herein, modifications as set forth herein include modified forms of melatonin. Accordingly, also provided are modified forms of melatonin. In a particular embodiment, melatonin can be coupled to a detectable label, tag or carrier via one or more various substituent groups. For example, a detectable label, tag or carrier can be attached to melatonin through the amino group in the indole ring, via a 5-methoxy derivative of melatonin. Such modified forms of melatonin can be used for detection of the labelled melatonin, such as in a method or use disclosed herein for detecting melatonin in a sample.

In various embodiments a detectable label, tag or carrier, can be bound or conjugated, either directly or indirectly, to an antibody, fragment thereof, or VH or VL chain of an antibody, or melatonin. Alternatively, a linker or an intermediary functional group can be used to link the detectable label or tag to an antibody, fragment thereof, or VH or VL chain of an antibody, or melatonin. A "linker" as used herein can mean, for example, a chemical moiety that joins two or more other chemical moieties via a covalent or non-covalent (e.g., ionic) bond.

Linkers include amino acid or peptidomimetic sequences inserted between an antibody, fragment thereof, or VH or VL chain of the antibody, or melatonin, and a label, tag or carrier so that the two entities maintain, at least in part, a distinct function or activity. Linkers may have one or more properties that include a flexible conformation, an inability to form an ordered secondary structure or a hydrophobic or charged character which could promote or interact with either domain. Amino acids typically found in flexible protein regions include Gly, Asn and Ser. Other near neutral amino acids, such as Thr and Ala, may also be used in the linker sequence. The length of the linker sequence may vary without significantly affecting a function or activity (e.g., target binding function or activity).

Linkers also include linear carbon chains, which can be represented by the formula $C_X$, where X is the number of carbons in the chain. Accordingly, carbon chains of any length can comprise a linker. A typical carbon chain linker has a length of about $C_1$-$C_{24}$.

Linkers further include chemical moieties, conjugating agents, and intermediary functional groups. Examples include moieties that react with free or semi-free amines, oxygen, sulfur, hydroxy or carboxy groups. Such functional groups therefore include mono and bifunctional crosslinkers, such as sulfo-succinimidyl derivatives (sulfo-SMCC, sulfo-SMPB), in particular, disuccinimidyl suberate (DSS), BS3 (Sulfo-DSS), disuccinimidyl glutarate (DSG) and disuccinimidyl tartrate (DST). Non-limiting examples include diethylenetriaminepentaacetic acid (DTPA) and ethylene diaminetetracetic acid.

Antibodies, fragments thereof, and VH and VL chains of an antibody can be produced using genetic techniques including expression of all or a part of the coding sequence into a host cell. Melatonin binding antibodies can be generated using techniques including hybridoma technology, recombinant, and phage display technologies, or a combination thereof (see U.S. Pat. Nos. 4,902,614, 4,543,439, and 4,411,993; see, also *Monoclonal Antibodies, Hybridomas: A New Dimension in Biological Analyses*, Plenum Press, Kennett, McKearn, and Bechtol (eds.), 1980, and Harlow et al., *Antibodies: A Laboratory Manual*, Cold Spring Harbor Laboratory Press, 2nd ed. 1988). Melatonin binding monoclonal antibodies can also be obtained by direct cloning of immunoglobulin sequences from animals, including mammals such as rabbit, primate or human subjects.

Animals may be immunized with melatonin, including rabbits, mice, rats, sheep, cows or steer, goats, pigs, horse, guinea pigs, and primates including humans, in order to obtain antibodies that bind to melatonin. "Immunizing" as used herein can refer to, for example, the stimulation of an immune response in an animal, such as a mammal (e.g., a rabbit), that can induce the production of antibodies. For example, immunizing can include exposing an animal to or contacting or injecting an animal with a substance, compound, or molecule.

Animals that may be immunized include genetically modified non-human animals having human IgG gene loci (e.g., lambda or kappa light chain), which are capable of expressing human antibodies. Transgenic animals with one or more human immunoglobulin genes (kappa or lambda) that do not express endogenous immunoglobulins are described, for example in, U.S. Pat. No. 5,939,598. Such animals can therefore be used to produce human antibodies. Additional methods for producing human polyclonal antibodies and human monoclonal antibodies are described (see, e.g., Kuroiwa et al., *Nat. Biotechnol.* 20:889 (2002); WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598). An overview of the technology for producing human antibodies is described in Lonberg and Huszar (*Int. Rev. Immunol.* 13:65 (1995)).

Antibody fragments can also be produced by proteolytic hydrolysis. An antibody, for example, can be digested with pepsin or papain. Antibody fragments produced by enzymatic cleavage with pepsin provide a 5S fragment denoted $F(ab')_2$. This fragment can be further cleaved using a thiol reducing agent to produce 3.5S Fab' monovalent fragments. Alternatively, an enzymatic cleavage using pepsin produces two monovalent Fab' fragments and the Fc fragment directly (see, e.g., U.S. Pat. Nos. 4,036,945 and 4,331,647; and Edelman et al., *Methods Enymol.* 1:422 (1967)). Other methods of cleaving antibodies, such as separation of heavy chains to form monovalent light-heavy chain fragments, further cleavage of fragments, or other enzymatic or chemical may also be used. Single-chain Fvs and antibodies can be produced as described in U.S. Pat. Nos. 4,946,778 and 5,258,498; Huston et al., *Methods Enzymol.* 203:46 (1991); Shu et al., *Proc. Natl. Acad. Sci. USA* 90:7995 (1993); and Skerra et al., *Science* 240:1038 (1988).

Antibodies can be humanized using a variety of techniques known in the art including, for example, CDR-grafting (EP 239,400; WO91/09967; U.S. Pat. Nos. 5,225,539; 5,530,101; and 5,585,089), veneering or resurfacing (EP 592,106; EP 519,596; Padlan, *Molecular Immunol.* 28:489 (1991); Studnicka et al., *Protein Engineering* 7:805 (1994); Roguska. et al., *Proc. Nat'l. Acad. Sci. USA* 91:969 (1994)), and chain shuffling (U.S. Pat. No. 5,565,332). Human consensus sequences (Padlan, *Mol. Immunol.*31:169 (1994); and Padlan, *Mol. Immunol.* 28:489 (1991)) can be used to humanize antibodies (Carter et al., *Proc. Natl. Acad. Sci. USA* 89:4285 (1992); and Presta et al., *J. Immunol.* 151:2623 (1993)).

Methods for producing chimeric antibodies are known in the art (e.g., Morrison, *Science* 229:1202 (1985); Oi et al., *BioTechniques* 4:214 (1986); Gillies et al., *J. Immunol. Methods* 125:191 (1989); and U.S. Pat. Nos. 5,807,715; 4,816,567; and 4,816,397). Chimeric antibodies in which a variable domain from an antibody of one species is substituted for the variable domain of another species are described, for example, in Munro, *Nature* 312:597 (1984); Neuberger et al., *Nature* 312:604 (1984); Sharon et al., *Nature* 309:364 (1984); Morrison et al., *Proc. Nat'l. Acad. Sci. USA* 81:6851 (1984); Boulianne et al., *Nature* 312:643 (1984); Capon et al., *Nature* 337:525 (1989); and Traunecker et al., *Nature* 339:68 (1989).

Modifications of antibodies, fragments thereof, and VH and VL chains of an antibody can be produced using methods known in the art (e.g., PCR based site-directed mutagenesis, substitution, addition/insertion or deletion, chemical modification and mutagenesis, or chemical cross-linking, etc.). For example, substitutions, additions/insertions, and deletions to a nucleic acid sequence encoding an antibody, fragment thereof, or VH or VL chain of an antibody. Further, deletion of one or more amino acids can also result in a modification of the structure without significantly altering a biological function or activity. Deletion of amino acids can lead to a smaller active molecule.

For methods and uses of the invention for determining, detection, measuring, screening for, analysis or monitoring, contact as used herein includes in solution, in solid phase, in situ, in vitro, ex vivo, such as a sample that potentially includes melatonin, in vivo, in vitro, or ex vivo. Contacting as used herein therefore includes in solution, in solid phase, in vitro, ex vivo, in a cell and in vivo.

The term "contacting" means direct or indirect interaction between two or more entities (e.g., between an antibody, fragment thereof, or VH or VL chain of an antibody and a target such as melatonin). A particular example of interaction is binding.

The term "bind," or "binding," when used in reference to an interaction between antibody (e.g., monoclonal antibody), fragments thereof and VH and VL chains of antibody and a target such as melatonin, means that there is a physical interaction at the molecular level or functional interaction between the antibody, fragment thereof, or VH or VL chain of the antibody. "Binding" as used herein can be due to an attraction between atoms, chemical moieties, or molecules, such as an attraction associated with the formation of hydrogen bonds, electrostatic interactions, dipole-dipole interactions, London dispersion interactions, cation-pi interactions, hydrophobic interactions, and hydrophilic interactions.

"Specific binding" as used herein can refer to selective or preferential binding of an antibody to a particular target that is present in a mixture of different targets. Typically, specific binding is that which is selective for a target, i.e., is statistically significantly higher than the background or control binding for the assay. Furthermore, binding to a non-target that does not significantly interfere with binding to a target is also considered specific.

Specific binding can be distinguished from non-specific binding using specificity, affinity, and competitive and non-competitive binding assays, described herein or known in the art (e.g., immunoprecipitation, enzyme-linked immunosorbant assay (ELISA), flow cytometry, immunohistochemistry, Western blotting, radioimmunoassay (RIA), immunoprecipitation, surface plasmon resonance, chemiluminescence, absorption, emission, fluorescent polarization, phosphorescence, or microarray). For example, when performing an immunoassay, controls typically include a reaction well/tube that contains an antibody or antigen binding fragment alone (i.e., in the absence of a sample or a sample that lacks melatonin), wherein an amount of reactivity (e.g., non-specific binding to the well) by the antibody or antigen binding fragment thereof in the absence of the sample or in the absence of melatonin is considered to be background.

As used herein, the terms "polynucleotide" and "nucleic acid" are used interchangeably to refer to all forms of nucleic acid, oligonucleotides, primers, and probes, including deoxyribonucleic acid (DNA) and ribonucleic acid (RNA). Polynucleotides include genomic DNA, cDNA and antisense DNA, and spliced or unspliced mRNA, rRNA tRNA and antisense RNA (e.g., RNAi). Polynucleotides include naturally occurring, synthetic, and intentionally altered or modified polynucleotides as well as analogues and derivatives. Alterations can result in increased stability due to resistance to nuclease digestion, for example.

The invention also provides polynucleotides encoding an antibody, fragment thereof, or VH or VL chain of an antibody. In one embodiment, a polynucleotide sequence has about 65% or more identity (e.g., 70%, 75%, 80%, 85%, 90%, 95%, 96%, 97%, 98%, 99% or more) to a sequence encoding an antibody, fragment thereof, or VH or VL chain of an antibody.

The "percent (%) nucleotide sequence identity" with respect to a nucleotide (i.e., nucleic acid or polynucleotide) sequence can be defined as the percentage of nucleotides in a candidate sequence that are identical with the nucleotides in the nucleic acid sequence to which comparison is made, after aligning the sequences and introducing gaps, if necessary, to achieve the maximum percent sequence identity. Where two nucleic acid sequences are identical, they have the same polynucleotide sequence, at least within the referenced region or portion.

In particular embodiments, a nucleic acid encodes amino acids of an antibody, fragment thereof, or VH or VL chain of an antibody. Such polynucleotides can therefore encode any sequence or any subsequence of an antibody, fragment thereof, or VH or VL chain of an antibody, such as one or more CDRs (e.g., any of SEQ ID NOs: 7-9 or 17-19).

Polynucleotides can be double, single or triplex, linear or circular, and can be of any length. In particular embodiments, polynucleotide sequences include sequences having 15-20, 20-30, 30-50, 50-75, 75-100, 100-150, 150-200, 200-250, 250-300, 300-400, 400-500 or more contiguous nucleotides.

Polynucleotides include sequences that are degenerate as a result of the genetic code. There are 20 natural amino acids, most of which are specified by more than one codon. Degenerate sequences may not selectively hybridize to other invention nucleic acids; however, they are nonetheless included as they encode an antibody, fragment thereof, or VH or VL chain of an antibody. Thus, in another embodiment, degenerate nucleotide sequences that encode an antibody, fragment thereof, or VH or VL chain of an antibody as set forth herein, are provided.

Polynucleotide sequences include complementary sequences (e.g., antisense to all or a part of an antibody, fragment thereof, or VH or VL chain of an antibody). Antisense may be encoded by a nucleic acid and such a nucleic acid may be operatively linked to an expression control element for sustained or increased expression of the encoded antisense in cells or in vivo.

The term "complementary" or "antisense" refers to a polynucleotide or peptide nucleic acid (PNA) capable of binding to a specific DNA or RNA sequence. Antisense includes single, double, triple or greater stranded RNA and DNA polynucleotides and peptide nucleic acids (PNAs) that bind RNA transcript or DNA. Particular examples include RNA and DNA antisense that binds to sense RNA and DNA. Antisense molecules are typically 90-100% complementary to the sense strand but can be "partially" complementary, in which only some of the nucleotides bind to the sense molecule (less than 100% complementary, e.g., 95%, 90%, 80%, 70% and sometimes less), or any numerical value or range within or encompassing such percent values.

Polynucleotides can be obtained using various standard cloning and chemical synthesis techniques. Purity of polynucleotides can be determined through sequencing, gel electrophoresis and the like. For example, nucleic acids can be isolated using hybridization as set forth herein or computer-based database screening techniques known in the art. Such techniques include, but are not limited to: (1) hybridization of genomic DNA or cDNA libraries with probes to detect homologous nucleotide sequences; (2) antibody screening to detect polypeptides having shared structural features, for example, using an expression library; (3) polymerase chain reaction (PCR) on genomic DNA or cDNA using primers capable of annealing to a nucleic acid sequence of interest; (4) computer searches of sequence databases for related sequences; and (5) differential screening of a subtracted nucleic acid library.

Antibody, fragments thereof, or VH or VL chain of an antibody polynucleotides can include an expression control element distinct from an endogenous antibody, fragment thereof, or VH or VL chain of an antibody gene (e.g., a non-native element), or exclude a control element from the native an antibody, fragment thereof, or VH or VL chain of an antibody gene to control expression of an operatively linked nucleic acid. Such polynucleotides containing an expression control element controlling expression of a nucleic acid can be modified or altered as set forth herein, so long as the modified or altered polynucleotide has one or more functions or activities.

As used herein, the term "recombinant," when used as a modifier of sequences such as polypeptides and polynucleotides, means that the compositions have been manipulated (i.e., engineered) in a fashion that generally does not occur in nature (e.g., in vitro). A particular example of a recombinant polypeptide would be where an antibody, fragment thereof, or VH or VL chain of an antibody is expressed by a cell transfected with a polynucleotide encoding the sequence. A particular example of a recombinant polynucleotide would be where a nucleic acid (e.g., genomic or cDNA) encoding an antibody, fragment thereof, or VH or VL chain of an antibody cloned into a plasmid, with or without 5', 3' or intron regions that the gene is normally contiguous with in the genome of the organism. Another example of a recombinant polynucleotide or polypeptide is a hybrid or fusion sequence, such as a chimeric antibody, fragment thereof, or VH or VL chain of an antibody comprising a second sequence, such as a heterologous functional domain.

For expression in cells, polynucleotides, if desired, may be inserted into a vector. Accordingly, invention compositions and methods further include polynucleotide sequences inserted into a vector.

The term "vector" refers to a nucleic acid molecule capable of transporting another nucleic acid molecule to which it has been linked. For example, a "plasmid" is a type of vector which has a circular, double-stranded DNA loop into which additional DNA segments may be ligated. A "phage vector" or a "viral vector" is a type of vector, which can have additional DNA segments ligated into a phage or viral genome. Such vectors can be used for genetic manipulation (i.e., "cloning vectors") or can be used to transcribe or translate the inserted polynucleotide (i.e., "expression vectors"). A vector generally contains at least an origin of replication for propagation in a cell and a promoter. Control elements, including expression control elements as set forth herein, present within a vector are included to facilitate proper transcription and translation (e.g., splicing signal for introns, maintenance of the correct reading frame of the gene to permit in-frame translation of mRNA and, stop codons etc.). Certain vectors can autonomously replicate in a host cell into which they are introduced. Certain vectors can be integrated into the genome of a host cell upon introduction into the host cell, so that they are replicated along with the host genome.

The term "host cell" can mean a biological cell in which a vector or expression vector can direct the production of proteins. For example, a host cell can be a prokaryotic or eukaryotic cell, such as a bacterial, a multicellular animal cell, or a mammalian (such as a rabbit) cell.

A hybridoma which produces an antibody can also be considered a host cell. A "hybridoma" as used herein can include a hybrid cell line in which a first cell is fused with a second cell that is different from the first cell. For example, an antibody-producing B cell can be fused with a cancerous B cell or a myeloma to form a hybridoma thereby providing an antibody producing cell line that can proliferate indefinitely. An "immortal cell" as used herein, can refer to, for example, a biological cell that can divide indefinitely, such as a cancer cell.

Invention antibodies, fragments thereof, and VH or VL chains of an antibody, methods and uses include pharmaceutical compositions, which refer to "pharmaceutically acceptable" and "physiologically acceptable" carriers, diluents or excipients. The term "pharmaceutically acceptable" and "physiologically acceptable," when referring to carriers, diluents or excipients includes solvents (aqueous or non-aqueous), detergents, solutions, emulsions, dispersion media, coatings, isotonic and absorption promoting or delaying agents, compatible with pharmaceutical administration.

Pharmaceutical compositions include water, aqueous solutions such as saline, fixed oils, polyethylene glycols, glycerine, propylene glycol or other synthetic solvents. The preparation may contain one or more preservatives to prevent microorganism growth (e.g., antibacterial agents), antioxidants, chelating agents; buffers and agents for the adjustment of tonicity. Pharmaceutical compositions can be formulated to be sterile.

The term "isolated," when used as a modifier of a composition, means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane. The term "isolated" does not exclude alternative physical forms, such as fusions/chimeras, multimers/oligomers, modifications (e.g., phosphorylation, glycosylation, lipidation) or derivatized forms, or recombinant or other forms expressed in vitro, in host cells, or in an animal and produced by the hand of man.

An "isolated" composition (e.g., antibody, fragment thereof, or VH or VL chain of the antibody) can also be "substantially pure" or "purified" when free of most or all of the materials with which it typically associates with in nature. Thus, an isolated sequence that also is substantially pure or purified does not include polypeptides or polynucleotides present among millions of other sequences, such as antibodies of an antibody library or nucleic acids in a genomic or cDNA library, for example. Typically, purity can be at least about 50%, 60% or more by mass. The purity can also be about 70% or 80% or more, and can be greater, for example, 90% or more. Purity can be determined by any appropriate method, including, for example, UV spectroscopy, chromatography (e.g., HPLC, gas phase), gel electrophoresis and sequence analysis (nucleic acid and peptide), and is typically relative to the amount of impurities, which typically does not include inert substances, such as water.

A "substantially pure" or "purified" composition can be combined with one or more other molecules. Thus, "substantially pure" or "purified" does not exclude combinations of compositions, such as combinations of antibody, fragment thereof, or VH or VL chains of antibody sequences, subsequences, variants and modified forms, and other molecular entities.

A "subject" refers to animals, typically mammalian animals, such as humans, non human primates (e.g., apes, gibbons, chimpanzees, orangutans, macaques), domestic animals (e.g., dogs and cats), farm animals (e.g., horses, cows, goats, sheep, pigs) and experimental animals (e.g., mouse, rat, rabbit, guinea pig). Subjects include animals that produce melatonin.

Subjects can be any age. For example, a subject (e.g., human) can be a newborn, infant, toddler, child, teenager, or an adult.

Non-limiting particular examples of subjects include those for which melatonin determination, detection, measurement, screening for, analysis or monitoring over a period of time is desired. Such subjects include those in need of a method or use of the invention, e.g., in need of melatonin. A subject is considered to be in need of a method or use of the invention where it is likely to provide information concerning the presence, amount or absence of melatonin in the subject.

As disclosed herein, an invention antibody, fragment thereof, or VH or VL chain of an antibody can be linked, affixed or adhered to a support or solid phase. Accordingly, an invention antibody, fragment thereof, or VH or VL chain of an antibody can be either in a free state, in solution or in solid phase, such as immobilized on a substrate or a support (e.g., solid).

Non-limiting examples of such formats include microtiter or multi-well plates or dishes, vials, tubes, inorganic sheets, dipsticks, a bead or sphere, or any other suitable substrate or support. Immobilization can be by passive adsorption (non-covalent binding) or covalent binding between the substrate or support and an invention antibody, fragment thereof, or VH or VL chain of an antibody, or indirectly by attaching an invention antibody, fragment thereof, or VH or VL chain of an antibody to a reagent which reagent is then attached to the substrate or support (e.g., a ligand-receptor system, for example, where a molecule is grafted onto the invention antibody, fragment thereof, or VH or VL chain of an antibody and the corresponding receptor immobilized on the substrate or support, as exemplified by the biotin-streptavidin system). An antibody, fragment thereof, or VH or VL chain of an antibody can be affixed to or contained in the support or substrate in a way that does not destroy function (e.g., target binding) of the antibody, fragment thereof, or VH or VL chain of an antibody absorbed thereon.

The support or substrate can be an inert material such as glass or plastic. One such material is an organic polymer such as polypropylene, which is chemically inert and hydrophobic, and has good chemical resistance to a variety of organic acids, organic agents, bases, salts, oxidizing agents, and mineral acids. Additional non-limiting examples include polyethylene, polybutylene, polyisobutylene, polybutadiene, polyisoprene, polyvinylpyrrolidine, polytetrafluroethylene, polyvinylidene difluoride, polyfluoroethylene-propylene, polyethylenevinyl alcohol, polymethylpentene, polycholorotrifluoroethylene, polysulfonones, hydroxylated biaxially oriented polypropylene, aminated biaxially oriented polypropylene, thiolated biaxially oriented polypropylene, etyleneacrylic acid, thylene methacrylic acid, nylons, and blends or copolymers thereof (e.g., blends of, alternating blocks of, or alternating components of, polypropylene, polyethylene, polybutylene, polyisobutylene, etc.).

The invention provides kits including antibody, fragment thereof, or VH or VL chain of an antibody and pharmaceutical formulations thereof, packaged into suitable packaging material. Kits can be used in various in vitro, ex vivo and in vivo methods and uses, for example a melatonin determination, detection, measurement, screen for, analysis or monitoring method or use as disclosed herein.

A kit typically includes a label or packaging insert including a description of the components or instructions for use in vitro, in vivo, or ex vivo, of the components therein. A kit can contain a collection of such components, e.g., an antibody, fragment thereof, or VH or VL chain of an antibody sequence alone, or in combination with another therapeutically useful composition.

The term "packaging material" refers to a physical structure housing the components of the kit. The packaging material can maintain sterility of the components, and can be made of material commonly used for such purposes (e.g., paper, corrugated fiber, glass, plastic, foil, ampules, vials, tubes, etc.). Invention kits can be designed for cold storage.

Kits of the invention can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., hard disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, amounts, etc. Labels or inserts can include information identifying manufacturer information, lot numbers, manufacturer location and date, recommended storage conditions, expiration date, etc.

Labels or inserts can include information on a method or use for which a kit component may be used. Labels or inserts can include instructions for the clinician or for a subject for using one or more of the kit components in a method or use, for example, as set forth herein. Instructions can include instructions for practicing any of the methods and uses set forth herein. Exemplary instructions include instructions for melatonin determination, detection, measurement, screening, analyzing or monitoring. Kits of the invention therefore can additionally include labels or instructions for practicing any of the methods and uses described herein.

Invention kits can additionally include other components. Each component of the kit can be enclosed within an individual container and all of the various containers can be within a single package. Invention kits can further be designed to contain antibody, fragment thereof, or VH or VL chain of an antibody, or combination compositions or pharmaceutical compositions.

The invention provides methods and uses of determining, detecting, measuring, screening for, assaying, analyzing and monitoring melatonin. The terms "determining," "measuring" "screening for," "assaying" and grammatical variations thereof are used interchangeably herein and refer to either qualitative or quantitative determinations, or both qualitative and quantitative determinations.

The methods and uses of the invention may be performed in solution, in solid phase, in silica, in vitro or in vivo. Typically, the invention methods and uses are performed in solution or in vitro.

Melatonin can be determined, detected, measured, screened for, analyzed or monitored for any duration. Melatonin can be determined, detected, measured, screened for, analyzed or monitored for any selected duration of time, for example, over a period of 24-48 hours, 16-24 hours, 12-16 hours, 8-12 hours, 6-8 hours, 4-6 hours, or less. For example, a sample suspected of containing melatonin can be provided, obtained or taken from a subject over a period of 24 hours, 16-24 hours, 12-16 hours, 8-12 hours, 6-8 hours, 4-6 hours, or less, and melatonin in each sample determined, detected, measured, screened for, analyzed or monitored for one or more of the selected time periods.

Melatonin can be determined, detected, measured, screened for, analyzed or monitored for any frequency. Melatonin can be determined, detected, measured, screened for, analyzed or monitored singly or multiple (e.g., 2, 3, 4, 5, 6, 7, 8, 9, 10, 11, 12, 13, 14, 15, 16, 17, 18, 19, 20 or more) times on the same day (e.g., every 1, 2, 3 or 4 hours, or other intervals such as every 15 minutes, 30 minutes, 60 minutes, 90 minutes, 120 minutes, 150 minutes, etc.), consecutive days, alternating days or intermittently. For example, a sample suspected of containing melatonin can be provided, obtained or taken 2, 3, 4, 5, 6, 7, 8, 9, 10, 11, 12, 13, 14, 15, 16, 17, 18, 19, 20 or more times daily, alternating days, bi-weekly, weekly, monthly, bi-monthly, and melatonin in each sample determined, detected, measured, screened for, analyzed or monitored.

Samples in which melatonin can be determined, detected, measured, screened for, analyzed or monitored include biological samples. Biological samples include any sample capable of having a biological material. Biological samples include any biological material from a subject. Non-limiting examples of biological samples include saliva, blood, serum, plasma, and mucus.

A biological sample can be stored in an environment to reduce loss of melatonin in the sample for example, due to degradation. Thus, a biological sample may be stored at a temperature less than ambient temperature, for example, at or less than 10 degrees Celsius (0-10 degrees Celsius), or less than 0 degrees Celsius.

A biological sample can also be processed or manipulated. For example, prior to determining, detecting, measuring, screening for, analyzing or monitoring melatonin, a biological sample can be diluted with a diluent. Exemplary diluents include, without limitation, Tris buffered saline (TBS) and phosphate buffered saline (PBS). Exemplary amounts of Tris (tris(hydroxymethyl)aminomethane) in a diluent are in a range of about 5 mM-200 mM, more typically about 25-100 mM. Exemplary amounts of phosphate in a diluent are in a range of about 1 mM-50 mM, more typically about 5-20 mM. Exemplary amounts of NaCl in a diluent are in a range of about 20 mM-500 mM, more typically about 50-200 mM.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

In disclosing embodiments and aspects herein, specific terminology is employed for the sake of clarity. However, the embodiments and aspects disclosed herein are not intended to be limited to the specific terminology so selected. A person skilled in the relevant art will recognize that other equivalent parts can be employed and other methods developed without parting from the spirit and scope of the embodiments and aspects.

As used herein, the singular forms "a", "and," and "the" include plural referents unless the context clearly indicates otherwise. Thus, for example, reference to "an antibody," "a fragment thereof," or "a VH or VL chain of an antibody" includes a plurality of such antibodies, fragments thereof, or VH or VL chains of an antibody, or combination compositions or pharmaceutical compositions.

As used herein, numerical values are often presented in a range format throughout this document. The use of a range format is merely for convenience and brevity and should not be construed as an inflexible limitation on the scope of the invention. Accordingly, the use of a range expressly includes all possible subranges, all individual numerical values within that range. Furthermore, all numerical values or numerical ranges include integers within such ranges and fractions of the values or the integers within ranges unless the context clearly indicates otherwise. This construction applies regardless of the breadth of the range and in all contexts throughout this patent document. Thus, for example, reference to a range of 6-48 hours or minutes includes 6-8, 6-10, 6-12, 6-14, 6-16, 6-18, 8-10, 8-12, 8-14, 8-16, 8-18, 8-20, 8-24, 10-12, 10-14, 10-16, 10-18, 10-20, 10-22, 10-24, and so forth. Reference to a range of 6-48 hours or minutes also includes 6-8, 6-10, 6-12, 6-14, 6-16, 6-18, 8-10, 8-12, 8-14, 8-16, 8-18, 8-20, 8-24, 10-12, 10-14, 10-16, 10-18, 10-20, 10-22, 10-24, and so forth.

In addition, the use of a series of ranges includes combinations of the upper and lower ranges to provide a range. This construction applies regardless of the breadth of the range and in all contexts throughout this patent document. Thus, for example, reference to a series of ranges such as 5 to 10, 10 to 20, 20 to 30, 30, to 50, 50 to 100, 100 to 150, 150 to 200, 200 to 300, or 300 to 400, 400-500, 500-600, or 600-705, includes ranges such as 5-20, 5-30, 5-40, 5-50, 5-75, 5-100, 5-150, 5-171, and 10-30, 10-40, 10-50, 10-75, 10-100, 10-150, 10-171, and 20-40, 20-50, 20-75, 20-100, 20-150, 20-200, 50 to 200, 50 to 300, 50, to 400, 50 to 500, 100 to 300, 100 to 400, 100 to 500, 100 to 600, 200-400, 200-500, 200 to 600, 200 to 700, and so forth.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

The embodiments illustrated and discussed in this specification are intended only to teach those skilled in the art how to make and use the invention. Nothing in this specification should be considered as limiting the scope of the embodiments disclosed herein. All examples presented are representative and non-limiting. The embodiments described herein may be modified or varied, as appreciated by those skilled in the art in light of the above teachings. It is therefore understood that, within the scope of the claims and their equivalents, the embodiments may be practiced otherwise than as specifically exemplified.

EXAMPLES

Example 1: This example includes a description of melatonin free acid synthesis and linking to a linker. (Reference: Australian Journal of Chemistry, 32, 399, 1979)

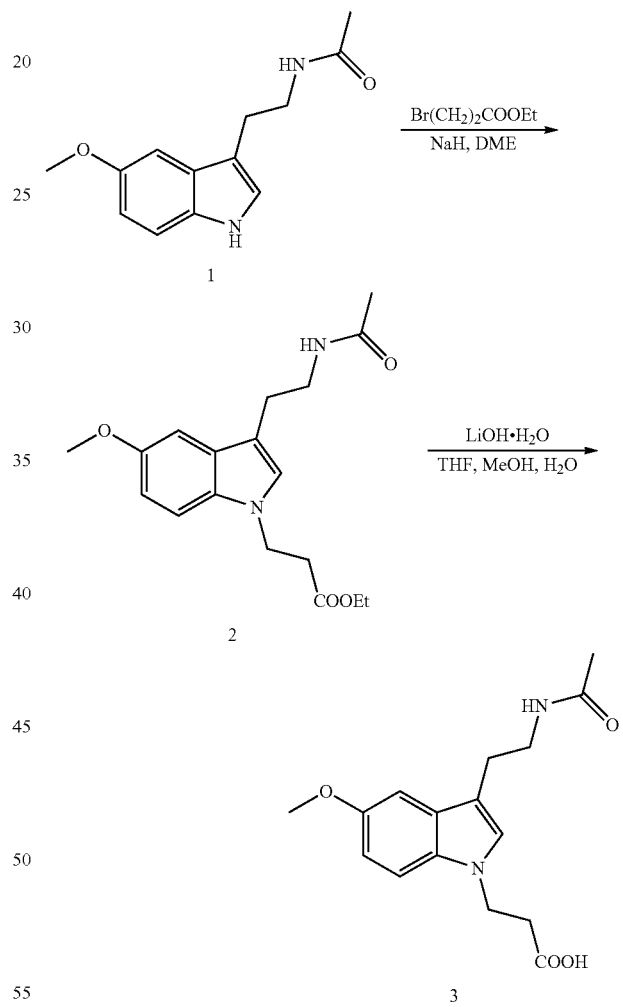

Step 1: To a suspension of NaH (60% in mineral oil, 1.94 g, 1.25 eq) in anhydrous DME (1,2-dimethoxyethane) (80 ml) was added dropwise a solution of melatonin, aka indole 1 (9 g, 1 eq) in anhydrous DME (100 ml). The resulting suspension was stirred at room temperature for 1 hour.

A solution of ethyl 3-bromopropionate (6.2 ml, 1.25 eq) in anhydrous DME (125 ml) was added dropwise and the reaction mixture was stirred at room temperature for three days. The reaction was quenched with aqueous $NH_4Cl$, was filtered through celite, dried over $Na_2SO_4$, and the solvent was evaporated. The residue was purified by flash chromatography to provide a mixture of starting material 1, product 2 and an unidentified bis adduct (2/10/4 ratio), as determined by $^1$H-NMR (nuclear magnetic resonance) and MS (mass spectrometry). The mixture was used in the next step without purification.

Step 2: The product from step 1 (ca. 14 g) was dissolved in a mixture of THF (tetrahydrofuran) (400 ml), methanol (100 ml), and water (100 ml). Lithium hydroxide monohydrate (5 g) was added and the resulting solution was stirred at room temperature for three days.

The solvent was evaporated and the residue was partitioned between brine and chloroform to remove compound 1. The aqueous phase was acidified using concentrated HCl and was extracted with chloroform. The organic phase was dried ($Na_2SO_4$) and the solvent was evaporated. The residue was purified by flash chromatography and trituration in hexanes to provide acid 3 as a white solid (4.95 g, 63% yield for two steps).

Example 2: This example includes a description of synthesis of melatonin-HRP conjugate.

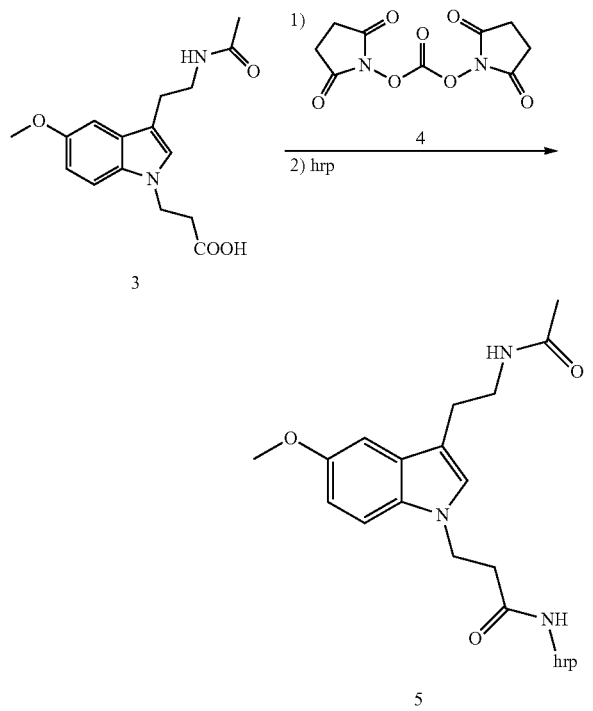

Solution A: In a dry 50 ml round-bottomed flask under $N_2$ was placed melatonin-propanoic acid linker, aka, compound 3 (9.9 mg, 0.0324 mmol), N,N-disuccinimidyl carbonate (4, 10.8 mg, 0.0421 mmol, 1.3 eq) and a $Et_3N$ solution in DMF (N,N-dimethylformamide) (100 µl/25 ml, 1.5 ml, 0.0421 mmol of base, 1.3 eq), and the resulting mixture was stirred for 30 min at room temperature.

Solution B: Horseradish peroxidase (HRP, 80 mg; 25KU, Sigma Lot #090M7715V) was dissolved in 2 ml of $H_2O$.

Reaction 1 (6:1 ratio*): 1 ml of solution B was added to 1 ml of solution A and the resulting solution was stirred at room temperature for three days.

Reaction 2 (3:1 ratio*): 1 ml of solution B was added to 0.5 ml of solution A and the resulting solution was stirred at room temperature for three days.

Purification: Each reaction was diluted with water (25 ml) and was extracted with a mixture of DCE(1,2-dichloroethane)/t-BuOH (63:37, 10 ml). This led to the formation of an emulsion which was centrifuged to separate the layers. This process was repeated five times until the unreacted steroid derivative was completely removed from the water layer. The absence of 3 from the water layer was monitored by MS. To the water layer was added 100 ml of water. In order to further purify the labelled HRP, the aqueous layer was subjected to tangential flow filtration (TFF) using water (1000 ml). TFF purification was continued until the final volume was 20 ml. The solution was transferred to a round-bottomed flask using water and was lyophilized to afford the HRP adducts 5 (30 mg and 33 mg for the reaction 1 and reaction 2 respectively). 6:1 ratio and 3:1 ratio refers to the approximate ratio between 3 and the free $NH_2$ groups in HRP.

Example 3: This example includes a description of a rabbit monoclonal antibody.

The Epitomics RabMab technology was used for development (U.S. Pat. Nos. 5,675,063 and 7,429,487). These patents present a method for generating a rabbit fusion partner cell line and antibodies produced from the cell line. Epitomics Rabbit fusion partner cells can fuse to rabbit B-cells to create the Rabbit Hybridoma cells. Hybridomas are then screened to select for clones with specific and sensitive antigen recognition and the antibodies are characterized using a variety of methods.

Monoclonal Screening

Eighty clones were selected based on the high dilutions required to achieve an endpoint on microplates coated with Melatonin-ovalbumin (a protein conjugate similar to KLH but intended as a carrier to help bind the Melatonin to the plate). Of these eighty clones, several were deselected due to their cross reactivity with related analogs: N Acetyl 5-Hydroxy Tryptamine (A), 5-Methoxy Tryptamine (B) and 6-Hydroxy Melatonin (C) and L-tryptophan (D) (these data are shown in section 4.5, cross-reactivity). The final clones were selected upon the ability to discriminate very low levels of melatonin (<1 pg/ml) in a competitive ELISA format.

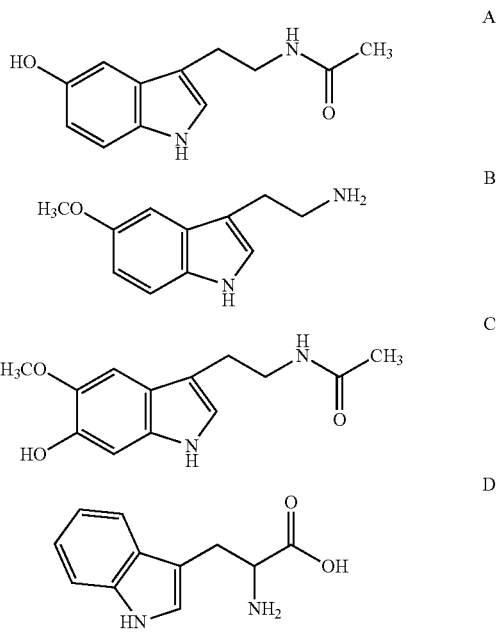

Rapid Melatonin ELISA (characterization of the performance of the rabbit monoclonal in order to define sensitivity).

A microtitre plate (described below) is coated with the rabbit monoclonal antibody to Melatonin. Melatonin in standards and unknowns competes with Melatonin linked to horseradish peroxidase for the antibody binding sites. After incubation unbound components are washed away. Bound Melatonin peroxidase is measured by the reaction of the peroxidase enzyme on the substrate tetramethylbenzidine (TMB). This reaction produces a blue color. A yellow color is formed after stopping the reaction with 2-molar sulfuric acid. Optical density is read on a standard plate reader at 450 nm. The amount of Melatonin peroxidase detected is inversely proportional to the amount of Melatonin present.

Microwell plates (CoStar High Binder) were coated overnight with 0.5 ug/ml goat anti-rabbit at room temperature [100 uL/well]; Coating Buffer-NaHCO$_3$ (2.93 g)+Na$_2$CO$_3$ (1.59 g) in 1000 ml Water, pH 9.6 under controlled humidity. After washing the plates 3 times in a wash buffer comprised of PBS (phosphate buffered saline) with 0.05% Tween 20, the plates were then coated with the rabbit monoclonal at 10 ng/ml in PBS with 0.01% BSA (bovine serum albumin) overnight at room temperature under controlled humidity. The plates were again washed and coated with 0.5% Stabilcoat (Surmodics) containing 0.1% normal rabbit serum. After approximately 2 hours the plates were aspirated, dried and pouched.

A primary dilution of Melatonin-HRP was made at 50 ug/ml in GUARDIAN® Conjugate stabilizer (Pierce-Thermo) for storage. At the time of the assay, it is then diluted to 100 ng/ml in a phosphate or Tris Buffered Saline, pH 7.2 with 1% BSA (Diluent).

Melatonin reference material from Cerilliant was diluted in diluent to 50 pg/ml. The standard curve was prepared by making 2× serial dilutions to 0.78 pg/ml in Diluent. Pipette: 100 ul Melatonin Standards/Samples/Controls to each well of the coated microwell plate. Pipette: 50 ul conjugate to each well. Incubate: 3 hr at 2-8° C. or Room Temperature with shaking (~500 rpm). Wash: 4×300 uL, no soak. Pipette: 100 uL tetramethylbenzidine (TMB). Incubate: Room Temp for 30 min with shaking. Pipette: 50 uL 2M H$_2$SO$_4$. Mix 10-15 seconds. Read Plate: OD 450-630 nm.

FIG. 1 shows the dose-response curve for the Rapid Melatonin assay (Salimetrics) compared to the overnight Bühlmann assay utilizing polyclonal antibodies. The reactivity closely match, indicating similarity of reactivity.

Saliva samples were tested with the Bühlmann and Rapid Salimetrics assays. The sensitivity of the Salimetrics and Bühlmann assay is similar, but the precision (% CV) of the rapid Salimetrics assay is better across the range than for the Bühlmann assay (Table 1).

TABLE 1

Precision

| Pg/ml Range | Salimetrics | | | Bühlmann | | |
|---|---|---|---|---|---|---|
| | N | % CV Avg. | % with CV above 15% | N | % CV Avg. | % with CV above 15% |
| 0.7 to 0.9 | 6 | 8% | 0% | 26 | 9% | 31% |
| 1 to 5 | 35 | 5% | 3% | 182 | 6% | 9% |
| 5 to 10 | 26 | 4% | 0% | 68 | 5% | 4% |
| 10 to 20 | 24 | 3% | 0% | 75 | 7% | 9% |
| 20 to 50 | 12 | 2% | 0% | 76 | 6% | 4% |

Accuracy in Saliva

Accuracy in saliva is determined by spike/recovery and dilution recovery of known levels of analyte in saliva. When a known level of analyte is added (spiked) into saliva, the detection of the amount that can be detected can be in the range of 80 to 120%. When saliva containing a known level of analyte is diluted in the appropriate buffer, the concentration detected can be in the range of 80-120% when corrected for the dilution factor. With variability inherent with saliva, an average dilution and/or spike recovery is taken into account for overall spike/dilution recovery. Table 2 below shows melatonin sample spike and recovery.

TABLE 2

Spike and Recovery

| Sample | Endogenous (pg/ml) | Added (pg/ml) | Expected (pg/ml) | Observed (pg/ml) | Returned Spike (pg/ml) | % Recovery |
|---|---|---|---|---|---|---|
| 1 | 2.3 | 33.9 | 36.2 | 40.3 | 38.0 | 112 |
| | 2.3 | 11.1 | 13.4 | 15.7 | 13.4 | 121 |
| | 2.3 | 5.2 | 7.5 | 8.5 | 6.2 | 119 |
| 2 | 1.9 | 33.9 | 35.8 | 39.3 | 37.4 | 110 |
| | 1.9 | 11.1 | 13.0 | 15.2 | 13.3 | 120 |
| | 1.9 | 5.2 | 7.1 | 7.7 | 5.8 | 111 |
| 3 | 13.6 | 11.1 | 24.7 | 25.9 | 12.3 | 110 |
| | 13.6 | 5.2 | 18.8 | 17.8 | 4.2 | 80 |

TABLE 3

Melatonin Sample Dilution Recovery

| Saliva Sample | Dilution | pg/ml | % CV | % Recovery |
|---|---|---|---|---|
| 1 | neat | 42.8 | 1.5 | |
| | 2X | 18.8 | 1.6 | 88 |
| 2 | neat | 39.9 | 1.5 | |
| | 2X | 18.5 | 3.3 | 93 |
| 3 | neat | 18.7 | 2.0 | |
| | 2X | 7.8 | 6.9 | 83 |
| 4 | neat | 15.2 | 1.2 | |
| | 2X | 6.9 | 8.1 | 91 |
| 5 | neat | 25.5 | 6.0 | |
| | 2X | 11.3 | 5.2 | 89 |

Cross Reactivity

Chemical compounds with structural similarity to melatonin were tested at levels 10 to 20-fold higher than the highest standard (50 pg/ml) as samples. The predicted value (as melatonin) was divided by the actual concentration added to calculate % cross-reactivity.

TABLE 4

Cross Reactivity (Specificity), Kit Insert

| Compound | Cross Reactivity (%) |
|---|---|
| Serotonin | <0.05 |
| N-acetyl serotonin | <0.05 |
| 5-methoxy tryptamine | <0.05 |
| 6-hydroxy melatonin | <0.05 |
| 5-methoxy tryptophol | 1.30% |
| 6-chloro melatonin | 5.40% |
| Caffeine | <0.05 |
| L-Tryptophan | <0.05 |
| AFMK | 16.5% |

AFMK = N$^1$-acetyl-N$^2$-formyl-5-methoxykynuramine

The second highest cross reactive compound, 6-chloro melatonin, is used as a melatonin receptor agonist, where the chlorine at the 6 position prevents oxidative metabolism. It is not expected to cause problems in normal analytical testing, unless an individual is undergoing specific therapy. The assay diluent was optimized to minimize interference from AFMK cross-reactivity.

Example 4: This example includes a description of sequencing a rabbit monoclonal antibody to melatonin.

The amino acid (peptide) sequence of the rabbit monoclonal antibody to melatonin, produced by hybridoma clone designated SLM-1-76-11 (clone SLM-1-76-4 also produced an antibody with the same sequence), was sequenced. The heavy chain variable region ($V_H$), light chain variable region ($V_L$), heavy chain constant region ($C_H$), and light chain constant region ($C_L$) of the antibody are set forth by the standard single-letter amino acid abbreviations in FIG. 2. The amino acid sequences are shown, from left to right, in the amino to carboxy direction. The complementarity determining regions (CDR) of the heavy chain are indicated by the bold, underlined letters (residues) in the $V_H$ sequence, and are labeled as CDR-H1, CDR-H2, and CDR-H3. The complementarity determining regions (CDR) of the light chain are indicated by the bold, underlined letters (residues) in the $V_L$ sequence, and are labeled as CDR-L1, CDR-L2, and CDR-L3.

The nucleotide (nucleic acid) sequence for the amino acid sequence of the rabbit monoclonal antibody to melatonin was determined. The nucleotide sequences are shown, from left to right, in the 5' to 3' direction. The nucleotide sequence coding for the heavy chain variable region and heavy chain constant region is set forth by the standard single-letter nucleotide abbreviations in FIG. 2. The portions of the nucleotide sequence coding for the complementarity determining regions (CDR) of the heavy chain and light chain for the start codon are indicated by the bold, underlined letters. A portion of the nucleotide sequence coding for the heavy chain constant region is shown with a regular (white) background. The portion of the nucleotide sequence coding for the light chain constant region is shown with a regular (white) background.

Example 5: This example includes a description of DLMO saliva collections and melatonin measurement and analysis.

The dim light melatonin onset (DLMO) is defined as the time when active melatonin secretion commences at night in subjects kept in dim light. Saliva samples were self-collected by 5 volunteer participants. After collection, the samples were immediately frozen.

The morning after the samples were collected; the samples were brought into the Salimetrics R&D Lab in an insulated container with a frozen BlueIce™ pack. All of the samples (5×13=65) were thawed and tested in duplicates with the Buhlmann Direct Saliva Melatonin ELISA (REF EK-SSM, Lot 4322) and the Salimetrics Salivary Melatonin Immunoassay kit (Item 3402, Lot 1305508) according to the kit insert instructions (listed in part in Example 6).

The predicted melatonin levels were summarized according to donor and kit results. In addition, the data was normalized between the two assay results because the background levels were significantly different. Normalized values were calculated by dividing the time-point pg/ml result by the average pg/ml result for each donor across all of the time-points.

Calculations of DLMO were made with a modification of method #3 which was described by Voultsios, Kennaway and Dawson (ref 1). Briefly, the DLMO was calculated as the mean plus 2 standard deviations of the first 3 time-point samples collected. The original paper described using samples collected at 19:00, 19:39 and 20:00. This assumes that the participant's normal bed times are all the same. Instead we asked that the participants count back 5 hours from their normal bed time.

All of the data are shown in FIGS. 4A-4E. Each table has the DLMO calculated for that donor as calculated separately for each test method. Briefly, the DLMO was calculated as the mean plus 2 standard deviations of the first 3 time-point samples collected, Normalized values were calculated by dividing the time-point pg/ml result by the average pg/ml result for each donor across all of the time-points. It should be noted that the normalized data yielded the same DLMO as that calculated with the raw pg/ml values. The data shown in the following table compares the DLMO times calculated for each donor by each assay

TABLE 5

| Donor | DLMO Time | |
|---|---|---|
| | DLMO Time, Salimetrics DLMO (hrs.) | DLMO Time, Buhlmann DLMO (hrs.) |
| C | 2.71 | 2.94 |
| D | 3.43 | 3.04 |
| F | 3.82 | 3.85 |
| I | 1.61 | 1.77 |
| J | 3.56 | 3.85 |

Note:
tested with PBS, 0.25M NaCl, 0.1% Tween-20, 0.5% BSA and 0.03%-0.05% ProClin.

The Salimetrics assay can be used to calculate DLMO. Results show no significant difference to those obtained using the Buhlmann assay. An added benefit over other melatonin assays is that the Salimetrics assay has a broader dynamic range.

Example 6: This example includes a description of kit insert assay instructions and components for salivary melatonin measurement and analysis.

Figure 3:
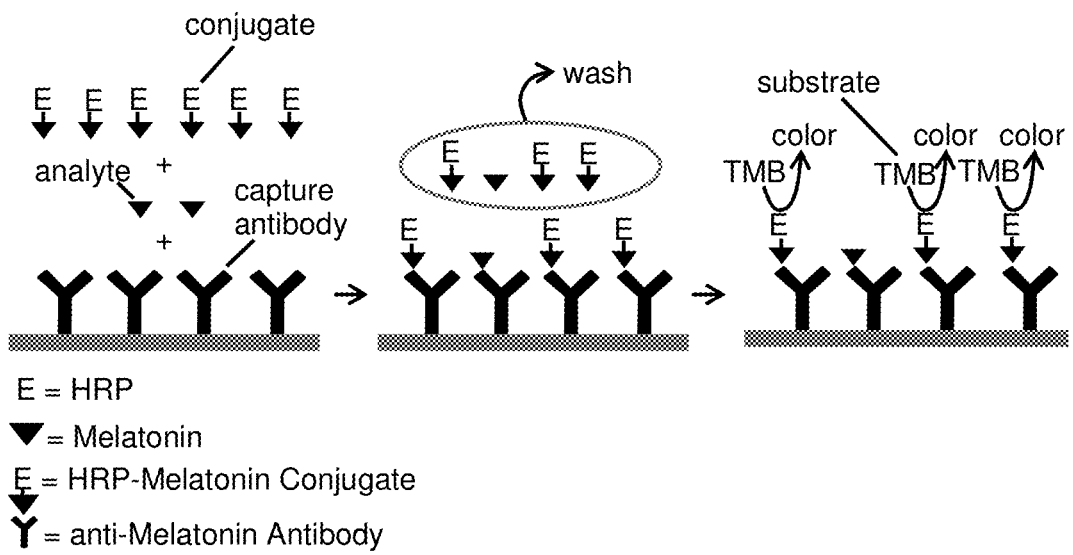
FIG. 3 shows an exemplary melatonin assay format using an anti-melatonin antibody.

The Salimetrics™ Salivary Melatonin kit is a competitive immunoassay designed and validated for the quantitative measurement of salivary melatonin. The assay format and detection method are illustrated in FIG. 3, and are briefly summarized as follows: A microtitre plate is coated with rabbit monoclonal antibody to melatonin. Melatonin in standards, controls and unknowns compete with melatonin linked to horseradish peroxidase for the antibody binding sites on the microplate. After incubation, unbound components are washed away. Bound melatonin peroxidase is measured by the reaction of the horseradish peroxidase enzyme with the substrate tetramethylbenzidine (TMB). This reaction produces a blue color. A yellow color is formed after stopping the reaction with 2-molar acid solution. Optical density is read on a standard microplate reader at 450 nm-630 nm. The amount of melatonin-tagged peroxidase detected, as measured by the intensity of color, is inversely proportional to the amount of melatonin present in the sample.

The following are noted in the kit insert:

The kit uses break-apart microtitre strips. You may run less than a full plate. Unused wells to be stored at 2-8° C. in the foil pouch with desiccant and used in the frame provided.

The quantity of reagent provided with a single kit is sufficient for two partial runs. The volumes of wash buffer and conjugate prepared for assays using less than a full plate should be scaled down accordingly, keeping the same dilution ratio.

Recommend to not mix components from different lots of kits.

When using a multichannel pipette to add reagents, follow the same sequence when adding all reagents so that the incubation time is the same for all wells.

To ensure highest quality assay results, pipetting of samples and reagents performed as quickly as possible (without interruption) across the plate. Ideally, the process should be completed within 20 minutes.

When running multiple plates, or multiple sets of strips, a standard curve must be run with each individual plate and/or set of strips.

The temperature of the laboratory may affect assays. Kits have been validated at 68-74° F. (20-23.3° C.). Higher or lower temperatures will cause an increase or decrease in OD values, respectively.

Avoid microbial contamination of opened reagents. Salimetrics recommends using opened reagents within one month. Store all reagents at 2-8° C.

Routine calibration of pipettes provides best possible assay performance.

When mixing plates during assay procedures, avoid speeds that spill the contents of the wells.

Reagent Preparation and Storage

Bring all reagents to room temperature and mix before use. A minimum of 1.5 hours is recommended for the 8 ml of melatonin assay diluent (conjugate dilution) to come to room temperature.

Bring microtitre plate to room temperature before use. Keep the foil pouch with the plate strips closed until warmed to room temperature, as humidity may have an effect on the coated wells.

Prepare 1× wash buffer by diluting wash buffer concentrate 10-fold with room-temperature deionized water (100 ml of wash buffer concentrate (10×) to 900 ml of deionized $H_2O$). Dilute only enough for current day's use, and discard any leftover reagent. (If precipitate has formed in the concentrated wash buffer, it may be heated to 40° C. for 15 minutes. Cool to room temperature before use in assay.)

Prepare serial dilutions of the Melatonin standard as follows:

Label six microcentrifuge tubes or other small tubes 2 through 7.

Pipette 300 μL of Melatonin Assay Diluent into tubes 2 through 7. Serially dilute the standard 2× by adding 300 μL of the 50 pg/ml standard (tube 1) to tube 2. Mix well (by vortexing ensuring no un-mixed dilution sample is trapped in the cap of the vial.) After changing pipette tips, transfer 300 μL from tube 2 to tube 3. Mix well. Continue for tubes 4, 5, 6 and 7. The final concentrations of standards for tubes 1 through 7, respectively, are 50 pg/ml, 25 pg/ml, 12.5 pg/ml, 6.25 pg/ml, 3.13 pg/ml, 1.56 pg/ml, and 0.78 pg/ml. Melatonin Assay Diluent is used for the Zero Standard.

Conversion: 1 pg/ml=4.3 pmol/L

All kit components are stable at 2-8° C. until the kit's expiration date.

Specimen Collection

Avoid sample collection within 60 minutes after eating a major meal or within 12 hours after consuming alcohol. Acidic or high sugar foods can compromise assay performance by lowering sample pH and influencing bacterial growth. To minimize such factors, rinse mouth thoroughly with water 10 minutes before sample is collected.

A preferred method for collecting whole saliva is by unstimulated passive drool. Donors may collect whole saliva by tilting the head forward, allowing the saliva to pool on the floor of the mouth, and then passing the saliva through the Saliva Collection Aid (SCA), Item No. 5016.02, into a polypropylene vial. Samples from adults and from children ages 6 and above may also be collected using the Salimetrics Oral Swab (SOS), Item No. 5001.02. Samples from children under the age of 6 may be collected with the Salimetrics Children's Swab (SCS), Item No. 5001.06. The Salimetrics Infant's Swab (SIS), Item No. 5001.08, is available for use with children under the age of 6 months. Detailed saliva collection information and collection protocols are available upon request or online at [[www.salimrics.com]]www-salimetrics-com.

Inaccurate readings may result if using Salivettes, sorbettes, cotton, or polyester materials to collect samples. Dipsticks may produce false positive values due to salivary enzymes.

Samples visibly contaminated with blood should be recollected. Samples may be screened for possible blood contamination (8, 9) using our Blood Contamination EIA Kit (Item Nos. 1-1302/1-1302-5).

Sample Handling and Preparation

After collection it is important to keep samples cold, to minimize bacterial growth in the specimen. Refrigerate sample within 30 minutes, and freeze at or below −20° C. within 4 hours of collection. (Samples may be stored at −20° C. for up to 6 months. For long term storage, >6 months, store at −60° C. or lower.) Melatonin levels will decrease ≥20% after 4 days at 2-8° C.

Do not add sodium azide to saliva samples as a preservative, as it may cause interference in the immunoassay.

Freezing saliva samples will precipitate mucins. On day of assay, thaw the saliva samples completely, vortex, and centrifuge at 1500×g (@3000 rpm) for 15 minutes. Centrifuging removes mucins and other particulate matter which may interfere with antibody binding, leading to falsely elevated results. Samples should be at room temperature before adding to assay plate. Pipette clear sample into appropriate wells. Re-freeze saliva samples as soon as possible after adding to the assay plate. Centrifuge/re-centrifuge saliva samples each time that they are thawed. Avoid more than 2 freeze-thaw cycles after the initial freeze/thaw.

TABLE 6

Materials Supplied with Single Kit

| | Item | Quantity/Size |
|---|---|---|
| 1 | Microtitre Plate Coated with rabbit anti-melatonin monoclonal antibodies†. | 1/96-well |
| 2 | Melatonin Standard in a Trizma buffered solution with stabilizer protein and a non-mercury preservative. Serially dilute before use according to Reagent Preparation. Higher order melatonin CRM*: 50 pg/ml | 1 vial, 1.5 ml |
| 3 | Melatonin Controls. High, Low, in a Trizma buffered solution with stabilizer protein and a non-mercury preservative. Refer to control insert for ranges. | 2 vials, 1 ml each |
| 4 | Wash Buffer Concentrate (10X). Dilute before use according to Reagent Preparation. Contains: phosphate buffer, detergent, preservative. | 1 bottle/100 ml |
| 5 | Melatonin Enzyme Conjugate Concentrate. Dilute before use with Melatonin Assay Diluent (see step 5 of Procedure). Contains: melatonin conjugated to HRP, buffer, preservative. | 1 vial/75 μL |

TABLE 6-continued

Materials Supplied with Single Kit

| Item | Quantity/Size |
|---|---|
| 6 Melatonin Assay Diluent. Ready to use. Contains a Trizma or PBS buffer with protein stabilizer and preservative | 1 bottle/30 ml |
| 7 TMB Substrate Solution Non-toxic, ready to use. | 1 bottle/25 ml |
| 8 2M Stop Solution Contains: sulfuric acid. | 1 bottle/12.5 ml |

Materials Needed But Not Necessarily Part of Kit
Precision pipettes to deliver 10 µL, to 300 µL,
Precision multichannel pipettes to deliver 50 µt, to 100 µt,
Vortex
Plate rotator with 0.08-0.17 inch orbit capable of 500 rpm
Plate reader with 450 nm and 620-630 nm reference filters
Computer software for data reduction
Deionized water
Reagent reservoirs
Disposable polypropylene tubes to hold at least 8 ml
Small disposable polypropylene tubes for dilution of standards
Pipette tips
Serological pipette to deliver up to 8 ml
Centrifuge capable of 1500×g (@3000 rpm)
Procedure
Step 1: Determine plate layout. The following plate layout may be used.

|   | 1 | 2 | 3 | 4 | 5 | 6 | 7 | 8 | 9 | 10 | 11 | 12 |
|---|---|---|---|---|---|---|---|---|---|---|---|---|
| A | 50 Std | 50 Std | C—H | C—H | | | | | | | | |
| B | 25 Std | 25 Std | C-L | C-L | | | | | | | | |
| C | 12.5 Std | 12.5 Std | Unk 1 | Unk 1 | | | | | | | | |
| D | 6.25 Std | 6.25 Std | Unk 2 | Unk 2 | | | | | | | | |
| E | 3.13 Std | 3.13 Std | Unk 3 | Unk 3 | | | | | | | | |
| F | 1.56 Std | 1.56 Std | Unk 4 | Unk 4 | | | | | | | | |
| G | 0.78 Std | 0.78 Std | Unk 5 | Unk 5 | | | | | | | | |
| H | 0 Std | 0 Std | Unk 6 | Unk 6 | | | | | | | | |

Step 2: Keep the desired number of strips in the strip holder and place the remaining strips back in the foil pouch. Reseal the foil pouch with unused wells and desiccant. Store at 2-8° C. Caution: Do not insert wells from one plate into a different plate.
Step 3: Pipette 8 ml of Melatonin Assay Diluent into a disposable tube. (Scale down proportionally if not using a full plate). Set aside for Step 5.
Step 4: Pipette 100 µL, of standards, controls, and unknown samples into appropriate wells. Standards, controls, and unknown samples should be assayed in duplicate.
Pipette 100 µL, of Melatonin Assay Diluent into 2 wells for the 0 Standard.
Step 5: Dilute the enzyme conjugate 1:500 by adding 16 µL of the conjugate to the 8 ml of melatonin assay diluent prepared in Step 3. (Scale down proportionally if not using the entire plate.) Conjugate tube may be centrifuged for a few minutes to bring the liquid down to the tube bottom. Immediately mix the diluted conjugate solution and add 50 µL to each well using a multichannel pipette.
Step 6: Place adhesive cover (provided) over plate. Mix plate constantly on a plate rotator at 500 rpm and incubate at 2-8° C. for a total of 3 hours.
Step 7: Wash the plate 4 times with 1× wash buffer. A plate washer is recommended. However, washing may be done by gently squirting wash buffer into each well with a squirt bottle, or by pipetting 300 µL, of wash buffer into each well and then discarding the liquid by inverting the plate over a sink. After each wash, the plate should be thoroughly blotted on paper towels before turning upright. If using a plate washer, blotting is still recommended after the last wash.
Step 8: Add 100 µL of TMB substrate solution to each well with a multichannel pipette.
Step 9: Incubate the plate in the dark at room temperature for 30 minutes mixing constantly on a plate rotator at 500 rpm.
Step 10: Add 50 µL of 2M stop solution with a multichannel pipette.
Step 11: Mix on a plate rotator for 3 minutes at 500 rpm. Spillage may occur if mixing speed exceeds 600 rpm. If green color remains, continue mixing until green color turns to yellow. Be sure all wells have turned yellow.
  Wipe off bottom of plate with a water-moistened, lint-free cloth and wipe dry.
  Read in a plate reader at 450 nm with a secondary filter at 620 to 630 nm. Performance characteristics are not known without secondary or reference filter. Read the plate within 10 minutes of adding 2M stop solution.
High and Low salivary Melatonin controls should be run with each assay. The control ranges established are to be used as a guide. Each laboratory should establish its own range. Variations between laboratories may be caused by differences in techniques and instrumentation.
  Calculations
  1. Compute the average optical density (OD) for all duplicate wells.
  2. Calculate the percent bound (B/Bo) for each standard, control and unknown by dividing the OD of each well (B) by the average OD for the 0 (Bo).
  3. Determine the concentrations of the controls and unknowns by interpolation using data reduction software. We recommend using a 4-parameter non-linear regression curve fit.
  4. Samples with Melatonin values greater than 50 pg/ml should be diluted further with Melatonin Assay Diluent and rerun for accurate results. If a dilution of the sample is used, multiply the results by the dilution factor. Dilution of a sample by more than 2-fold is not recommended.
When running multiple plates, or multiple sets of strips, a standard curve should be run with each individual plate and/or set of strips.
Typical Results

TABLE 7

Results shown below are for illustration only and should not be used to calculate results from another assay.

| Well | Sample | Average OD | B/Bo | Melatonin (pg/ml) |
|---|---|---|---|---|
| A1, A2 | S1 | 0.348 | 0.14 | 50.0 |
| B1, B2 | S2 | 0.754 | 0.31 | 25.0 |
| C1, C2 | S3 | 1.363 | 0.56 | 12.5 |
| D1, D2 | S4 | 1.868 | 0.77 | 6.25 |
| E1, E2 | S5 | 2.122 | 0.87 | 3.13 |
| F1, F2 | S6 | 2.238 | 0.92 | 1.56 |
| G1, G2 | S7 | 2.336 | 0.96 | 0.78 |
| H1, H2 | 0 | 2.427 | 1.00 | 0.0 |

Considerations
- Samples with Melatonin values greater than 50 pg/ml should be diluted further with Melatonin Assay Diluent and rerun for more accurate results. If a dilution of the sample is used, multiply the results by the dilution factor. Dilution of a sample by more than 2-fold not recommended.
- See Specimen Collection recommendations to insure proper collection of saliva specimens and to avoid interfering substances.
- Samples collected with sodium azide may interfere with accuracy.
- Avoid more than 2 freeze-thaw cycles after the initial freeze/thaw.

Salivary Melatonin Example Ranges and Method Comparison

Thirteen adult subjects collected their own saliva just before sleeping (PM), just after arising from sleep (AM) and in the middle of the day (Noon). Samples were frozen and transported to the testing laboratory. The samples were tested in duplicate with the Salimetrics Salivary Melatonin Immunoassay Kit and the Bühlmann Direct Saliva Melatonin ELISA. Q1=the 1$^{st}$ quartile where 25% of the results were less than or equal to the value and Q3=the 3$^{rd}$ quartile where 25% of the results were greater than or equal to the value (Tables 8 and 9). The correlation between the two methods was 0.78.

TABLE 8

Salivary Range Tested by Salimetrics and Buhlmann Methods

| | Salimetrics | | | | Buhlmann | | | P Value |
|---|---|---|---|---|---|---|---|---|
| Time | N | Median (pg/ml) | Q1 | Q3 | N | Median (pg/ml) | Q1 | Q3 | (Time: Salimetrics vs. Buhlmann) |
| AM | 13 | 6.5 | 3.4 | 12.3 | 35 | 11.7 | 8.3 | 17.4 | >0.05 |
| Noon | 12 | 3.9 | 1.6 | 5.6 | 46 | 3.3 | 1.8 | 6.0 | >0.05 |
| PM | 9 | 18.4 | 12.2 | 21.1 | 36 | 16.4 | 8.4 | 23.1 | >0.05 |

Note:
tested with PBS, 0.25M NaCl, 0.1% Tween-20, 0.5% BSA, and 0.03%-0.05% ProClin.

Precision

Intra-assay precision was determined from the mean of 20 replicates each sample (Table 9).

TABLE 9

| Saliva Sample | N | Mean pg/ml | Standard Deviation pg/ml | % CV |
|---|---|---|---|---|
| 1 | 20 | 44.3 | 1.2 | 2.7 |
| 2 | 20 | 25.9 | 1.3 | 5.0 |
| 3 | 20 | 13.5 | 0.5 | 3.5 |
| 4 | 20 | 8.0 | 0.4 | 5.4 |
| 5 | 20 | 4.0 | 0.4 | 9.7 |

The inter-assay precision was determined from the average of 20 replicates across 10 runs, replicates of 2 per run (Table 10).

TABLE 10

| Saliva Sample | N | Mean pg/ml | Standard Deviation pg/ml | % CV |
|---|---|---|---|---|
| 1 | 20 | 42.9 | 3.2 | 7.6 |
| 2 | 20 | 24.2 | 1.4 | 5.9 |
| 3 | 20 | 13.4 | 1.1 | 8.4 |

TABLE 10-continued

| Saliva Sample | N | Mean pg/ml | Standard Deviation pg/ml | % CV |
|---|---|---|---|---|
| 4 | 20 | 6.8 | 0.7 | 10.6 |
| 5 | 20 | 3.8 | 0.6 | 14.6 |

Recovery

Three saliva samples were spiked with different levels of Melatonin and assayed (Table 11). The recovery is based on the prediction of the spike (minus endogenous), not the total concentration.

TABLE 11

| Sample | Endogenous pg/ml | Added pg/ml | Expected pg/ml | Observed pg/ml | Returned Spike pg/ml | % Recovery |
|---|---|---|---|---|---|---|
| 1 | 2.3 | 33.9 | 36.2 | 40.3 | 38.0 | 112 |
| | 2.3 | 11.1 | 13.4 | 15.7 | 13.4 | 121 |
| | 2.3 | 5.2 | 7.5 | 8.5 | 6.2 | 119 |
| 2 | 1.9 | 33.9 | 35.8 | 39.3 | 37.4 | 110 |
| | 1.9 | 11.1 | 13.0 | 15.2 | 13.3 | 120 |
| | 1.9 | 5.2 | 7.1 | 7.7 | 5.8 | 111 |
| 3 | 13.6 | 11.1 | 24.7 | 25.9 | 12.3 | 110 |
| | 13.6 | 5.2 | 18.8 | 17.8 | 4.2 | 80 |

Sensitivity
Analytical Sensitivity

The lower limit of sensitivity was determined by interpolating the mean optical density minus 2 SDs of 10 sets of duplicates randomized across the plate within one run at the 0 pg/ml level. The minimal concentration of Melatonin that can be distinguished from 0 is 0.58 pg/ml.

Functional Sensitivity

The functional sensitivity was determined as the concentration of 11 saliva samples, tested as 20 replicates each, resulting in a CV of 30% or less. The functional sensitivity of the Salivary Melatonin EIA is 1.9 pg/ml.

Comparative Saliva Sample Precision

The coefficients of variance (CV's) from the example ranges study were compared between the two assays (Table 12). Thirteen subjects, three time points in duplicate. There were 3 results for the Bühlmann assay which were above the reportable range and were not included in the calculations.

TABLE 12

| Assay | N | Median % CV | Q1 % CV | Q3 % CV |
|---|---|---|---|---|
| Salimetrics | 39 | 2.2 | 1.2 | 4.5 |
| Bühlmann | 36 | 5.3 | 2.5 | 11.8 |

Sample Dilution Recovery

Five saliva samples of differing Melatonin concentrations were diluted in Melatonin Assay Diluent and assayed (Table 13).

TABLE 13

| Saliva Sample | Dilution | Mean pg/ml | % CV | % Recovery |
|---|---|---|---|---|
| 1 | neat | 42.4 | 1.5 | |
|   | 2X | 18.8 | 1.6 | 88.5 |
| 2 | neat | 39.8 | 1.5 | |
|   | 2X | 18.5 | 3.3 | 92.8 |
| 3 | neat | 18.6 | 2.0 | |
|   | 2X | 7.8 | 6.9 | 83.6 |
| 4 | neat | 15.0 | 1.2 | |
|   | 2X | 6.6 | 8.1 | 88.7 |
| 5 | neat | 26.8 | 6.0 | |
|   | 2X | 11.7 | 5.2 | 87.6 |

Dilution Linearity

Figure 5:
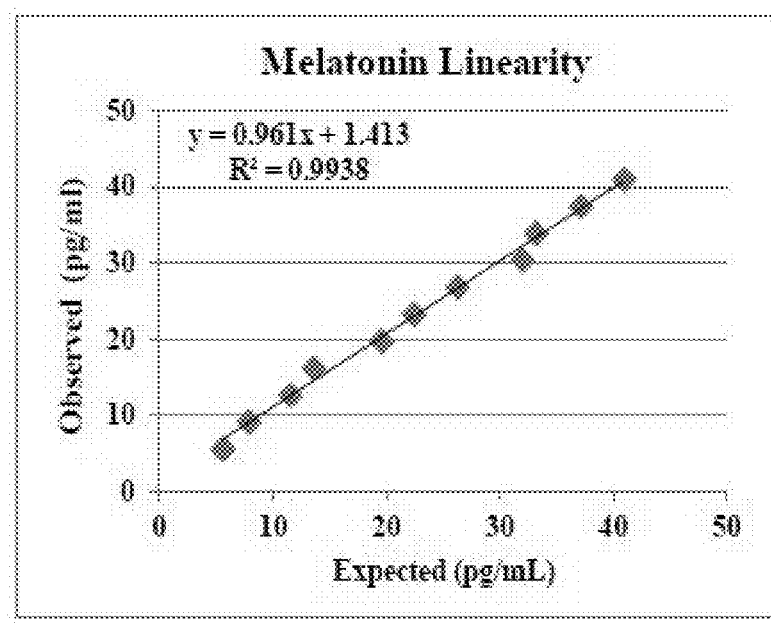
FIG. 5 shows an assay of a mixture of two saliva samples diluted with each other proportionately.

Two saliva sample were diluted with each other proportionately and assayed in replicates of two, as shown in FIG. 5.

Drift

Drift was determined by individually pipetting 96 wells of one Melatonin concentration in singlets across the plate and determining the CV of the optical densities for all wells. The CV resulting from this calculation was 3.97%

Specificity

Chemicals with structural similarities to melatonin were spiked into saliva to up to 2000 pg/ml and tested as samples. For cross reactants, the concentration of Melatonin at the EC50 (B/Bo=0.5) was divided by the concentration of the cross reactant at its EC50 (B/Bo=0.5) for the % cross reactivity (Table 14).

TABLE 14

| Compound | Cross Reactivity |
|---|---|
| Serotonin | <0.05% |
| N-acetyl serotonin | <0.05% |
| 5-methoxy tryptamine | <0.05% |
| 6-hydroxy melatonin | <0.05% |
| 5-methoxy tryptophol | 1.25% |
| 6-chloro melatonin | 5.40% |
| Caffeine | <0.05% |
| L-Tryphtophan | <0.05% |
| AFMK | 16.5% |

AFMK = $N^1$-acetyl-$N^2$-formyl-5-methoxykynuramine

REFERENCES

[1] Voultsios A, Kennaway D J and D Dawson. Salivary melatonin as a circadian phase marker: Validation and comparison to plasma melatonin. Journal of Biological Rhythms, 1997 12(5), 457-466

[2] Burgess H J and L F Fogg. Individual differences in the amount and timing of salivary melatonin secretion. PLoS One, 2008 3(8) e3055 doi:10.1371/journal.pone.0003055

[3] Hardeland R and S R Pandi-Perumal. Melatonin, a potent agent in antioxidative defense: Actions as a natural food constituent, gastrointestinal factor, drug and prodrug. Nutrition and Metabolism, 2005, 2, 22-36

[4] Tan D-X, Manchester L C, Terron M P, Flores L J and R J Reiter. One molecule, many derivatives: A never ending interaction of melatonin with reactive oxygen and nitrogen species? J. Pineal Res 2007, 42, 28-42

[5] Nowak R, McMillen I C, Redman J and R V Short. The correlation between serum and salivary melatonin concentrations and urinary 6-hydroxymelatonin sulphate excretion rates: Two non-invasive techniques for monitoring human circadian rhythmicity. Clinical Endocrinology, 1987, 27, 445-452

[6] de Almeida E A, Di Mascio P, Harumi T, Spence D W, Moscovitch A, Hardeland R, Cardinali D P, Brown G M and S R Pandi-Perumal. Measurement of melatonin in body fluids: Standards, protocols and procedures. Childs Nerv Syst, 2011, 27(6), 879-891

[7] Shirtcliff, E A, Granger, D A, Schwartz, E B, Nelson, V & M. Curran. Use of salivary biomarkers in biobehavioral research: Cotton-based sample collection methods can interfere with salivary immunoassay results. Psychoneuroendocrinology 2001, 26(2), 165-73

[8] Kivlighan K T, Granger D A, Schwartz E B, Nelson V and M. Curran. Quantifying blood leakage into the oral mucosa and its effects on the measurement of cortisol, dehydroepiandrosterone and testosterone in saliva. Hormones and Behavior 2004, 46, 39-46

[9] Schwartz E and D A Granger. Transferrin enzyme immunoassay for quantitative monitoring of blood contamination in saliva. Clinical Chemistry 2004, 50, 654-656

What is claimed is:

1. A monoclonal antibody or fragment thereof that specifically binds to melatonin, comprising: a heavy chain variable region comprising a CDR-H1 sequence comprising the sequence of SEQ ID NO:7, a CDR-H2 sequence comprising the sequence of SEQ ID NO:8, and a CDR-H3 sequence comprising the sequence of SEQ ID NO:9; and a light chain variable region comprising a CDR-L1 sequence comprising the sequence of SEQ ID NO:17, a CDR-L2 sequence comprising the sequence of SEQ ID NO:18, and a CDR-L3 sequence comprising the sequence of SEQ ID NO:19.

2. The monoclonal antibody or fragment thereof of claim 1, wherein the antibody comprises: a heavy chain variable region (VH) comprising a sequence with at least 95% sequence identity to the sequence of SEQ ID NO:6 outside the CDR-H1, CDR-H2, CDR-H3, CDR-L1, CDR-L2 and CDR-L3 sequences; and a light chain variable region ($V_L$) comprising a sequence with at least 95% sequence identity to the sequence of SEQ ID NO:16 outside the CDR-H1, CDR-H2, CDR-H3, CDR-L1, CDR-L2 and CDR-L3 sequences.

3. A heavy chain variable region (VH) comprising a CDR-H1 sequence comprising the sequence of SEQ ID NO:7, a CDR-H2 sequence comprising the sequence of SEQ ID NO:8, and a CDR-H3 sequence comprising the sequence of SEQ ID NO:9.

4. A light chain variable region (VL) comprising a CDR-L1 sequence comprising the sequence of SEQ ID NO:17, a CDR-L2 sequence comprising the sequence of SEQ ID NO:18, and a CDR-L3 sequence comprising h the sequence of SEQ ID NO:19.

5. The monoclonal antibody or fragment thereof of claim 1, wherein the VH or VL of the monoclonal antibody or fragment thereof has 1-5 amino acid substitutions outside the CDR-H1, CDR-H2, CDR-H3, CDR-L1, CDR-L2 and CDR-L3 sequences.

6. The monoclonal antibody or fragment thereof of claim 5, wherein the amino acid substitution is a conservative amino acid substitution.

7. The monoclonal antibody or fragment thereof of claim 1, wherein the VH or VL of the monoclonal antibody or fragment thereof has 1-5 conservative amino acid substitutions outside the CDR-H1, CDR-H2, CDR-H3, CDR-L1, CDR-L2 and CDR-L3 sequences of the heavy or the light chain variable region sequence.

8. The monoclonal antibody or fragment thereof of claim 1, wherein the monoclonal antibody or fragment or VH or VL comprises a rabbit monoclonal.

9. The monoclonal antibody or fragment thereof of claim 1, wherein the antibody or fragment thereof or VH or VL is humanized.

10. The monoclonal antibody or fragment thereof of claim 1, wherein the antibody or fragment thereof or the VH or VL comprises an Fab, Fab', F(ab')$_2$, Fv, Fd, single-chain Fv (scFv), disulfide-linked Fvs (sdFv), $V_L$, $V_H$, diabody ((VL-VH)2 or (VH-VL)$_2$), triabody (trivalent), tetra body (tetravalent), minibody ((scFv-CH3)$^2$), IgGdeltaCH2, scFv-Fc or (scFv)$_2$-Fc fragment.

11. The monoclonal antibody or fragment thereof of claim 1, wherein the antibody or fragment thereof or the VH or VL comprises an IgG, IgA, IgE, IgM or IgD isotype.

12. The monoclonal antibody or fragment thereof of claim 1, that specifically binds to melatonin with sensitivity to melatonin concentrations of less than or equal to about 1 pg/ml.

13. The monoclonal antibody or fragment thereof of claim 1, which does not specifically bind to N-acetyl-5-hydroxy-tryptamine, 5-methoxy-tryptamine, 6-hydroxy-melatonin, or L-tryptophan.

14. A monoclonal antibody-melatonin complex, comprising a monoclonal antibody or fragment thereof of claim 1 bound to melatonin.

15. A conjugate, comprising: the monoclonal antibody or fragment thereof of claim 1, and a detectable moiety, wherein the monoclonal antibody is linked to the detectable moiety.

16. The antibody conjugate of claim 15, wherein the detectable moiety is selected from the group consisting of an enzyme, horse radish peroxidase, alkaline phosphatase, glucose oxidase, glucose-6-phosphate dehydrogenase, ma late dehydrogenase, staphylococca I nuclease, delta-V-steroid isomerase, yeast alcohol dehydrogenase, alpha-glycerophosphate, dehydrogenase, triose phosphate isomerase, asparaginase, beta-galactosidase, ribonuclease, urease, catalase, glucoamylase, acetylcholinesterase, biotin, iminobiotin, a fluorophore, a fluorescent protein, chromophore, chemiluminescent material, phosphorescent material, an electrochemiluminescent tag, and a radionucleotide.

17. A composition comprising the monoclonal antibody or fragment thereof of claim 1.

18. A host cell that produces the monoclonal antibody or fragment thereof of claim 1.

19. A method for producing the monoclonal antibody or fragment thereof of claim 1, comprising: culturing in suitable medium and culture conditions a host cell expressing the monoclonal antibody or fragment thereof of claim 1, so that the antibodies or fragments thereof are produced; and recovering the produced antibodies or fragments thereof from the culture medium and/or from the host cells.

20. The host cell of claim 18, wherein the host cell comprises a hybridoma.

* * * * *

SEQUENCE LISTING

```
<160> NUMBER OF SEQ ID NOS: 20

<210> SEQ ID NO 1
<211> LENGTH: 429
<212> TYPE: DNA
<213> ORGANISM: Artificial Sequence
<220> FEATURE:
<223> OTHER INFORMATION: Description of Artificial Sequence: Heavy chain
      antibody

<400> SEQUENCE: 1
atggagactg ggctgcgctg gcttctcctg gtcgctgtgc tcaaaggtgt ccagtgtcag       60
tcgttggagg agtccggggg agacctggtc aagcctgggg catccctgac actcacctgc     120
acagcctctg gattctcttt tagtcgctat gattatatgt gctgggtccg ccaggctcca     180
gggaaggggc tggagtggat cgcaagtatt tatgttggta gtggtgtcac ttactactcg     240
```

```
acctgggcga gaggccgatt cgccatctcc caaacctcgt cgaccacgat gactctacaa    300
atgaccagtc tgacagccgc ggacacggcc acttacttct gtgcgagatt tcatggtcat    360
ggtggtggtg attatgctct gggggctttt gatccctggg gcccaggcac cctggtcacc    420
gtctcctca                                                            429
```

```
<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: CDR
      fragment

<400> SEQUENCE: 2
cgctatgatt atatgtgc                                                   18

<210> SEQ ID NO 3
<211> LENGTH: 51
<212> TYPE: DNA
<213> ORGANISM: Artificial Sequence
<220> FEATURE:
<223> OTHER INFORMATION: Description of Artificial Sequence: CDR
      fragment

<400> SEQUENCE: 3
agtatttatg ttggtagtgg tgtcacttac tactcgacct gggcgagagg c              51

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence: CDR
      fragment

<400> SEQUENCE: 4
tttcatggtc atggtggtgg tgattatgct ctgggggctt ttgatccc                  48

<210> SEQ ID NO 5
<211> LENGTH: 98
<212> TYPE: DNA
<213> ORGANISM: Artificial Sequence
<220> FEATURE:
<223> OTHER INFORMATION: Description of Artificial Sequence: Heavy chain
      antibody

<400> SEQUENCE: 5
gggcaaccta aggctccatc agtcttccca ctggcccct gctgcgggga cacacccagc     60
tccacggtga ccctgggctg cctggtcaaa gggtacct                             98

<210> SEQ ID NO 6
<211> LENGTH: 143
<212> TYPE: PRT
<213> ORGANISM: Artificial Sequence
<220> FEATURE:
<223> OTHER INFORMATION: Description of Artificial Sequence: Heavy chain
      antibody

<400> SEQUENCE: 6

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30
```

Gly Ala Ser Leu Thr Leu Thr Cys Thr Ala Ser Gly Phe Ser Phe Ser
            35                  40                  45

Arg Tyr Asp Tyr Met Cys Trp Val Arg Gln Ala Pro Gly Lys Gly Leu
 50                  55                  60

Glu Trp Ile Ala Ser Ile Tyr Val Gly Ser Gly Val Thr Tyr Tyr Ser
 65                  70                  75                  80

Thr Trp Ala Arg Gly Arg Phe Ala Ile Ser Gln Thr Ser Thr Thr
                85                  90                  95

Met Thr Leu Gln Met Thr Ser Leu Thr Ala Ala Asp Thr Ala Thr Tyr
            100                 105                 110

Phe Cys Ala Arg Phe His Gly His Gly Gly Gly Asp Tyr Ala Leu Gly
            115                 120                 125

Ala Phe Asp Pro Trp Gly Pro Gly Thr Leu Val Thr Val Ser Ser
        130                 135                 140

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Heavy chain
      antibody fragment

<400> SEQUENCE: 7

Arg Tyr Asp Tyr Met Cys
1               5

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence:  Heavy
      chain antibody fragment

<400> SEQUENCE: 8

Ser Ile Tyr Val Gly Ser Gly Val Thr Tyr Tyr Ser Thr Trp Ala Arg
1               5                   10                  15

Gly

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence:  Heavy
      chain antibody fragment

<400> SEQUENCE: 9

Phe His Gly His Gly Gly Gly Asp Tyr Ala Leu Gly Ala Phe Asp Pro
1               5                   10                  15

<210> SEQ ID NO 10
<211> LENGTH: 32
<212> TYPE: PRT
<213> ORGANISM: Artificial Sequence
<220> FEATURE:
<223> OTHER INFORMATION: Description of Artificial Sequence:  Heavy
      chain constant region

<400> SEQUENCE: 10

Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
            20                  25                  30

<210> SEQ ID NO 11
<211> LENGTH: 396
<212> TYPE: DNA
<213> ORGANISM: Artificial Sequence
<220> FEATURE:
<223> OTHER INFORMATION: Description of Artificial Sequence: Light chain
      antibody

<400> SEQUENCE: 11
atggacacga gggcccccac tcagctgctg gggctcctgc tgctctggct cccaggtgcc      60
agatgtgcct atgatatgac ccagactcca gcctccgtgt ctgcagctgt gggaggcaca     120
gtcaccatca attgccaggc cagtcagagc atcagcaacc tcttagcctg gtatcagcag     180
aaaccagggc agcctcccaa gctcctgatc tattctgcat ccactctggc atctggggtc     240
ccatcgcggt tcaaaggcag tggatctggg acacagttca ctctcaccat cagcgacctg     300
gagtgtgccg atgctgccac ttactactgt cagcagggtt atgatggtat tggtgttgta     360
aattttttcg gcggagggac cgaggtggtg gtcaaa                               396

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Light chain
      antibody fragment

<400> SEQUENCE: 12
caggccagtc agagcatcag caacctctta gcc                                   33

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Light chain
      antibody fragment

<400> SEQUENCE: 13
tctgcatcca ctctggcatc t                                                21

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Light chain
      antibody fragment

<400> SEQUENCE: 14
cagcagggtt atgatggtat tggtgttgta aatttt                                36

<210> SEQ ID NO 15
<211> LENGTH: 315
<212> TYPE: DNA
<213> ORGANISM: Artificial Sequence
<220> FEATURE:
<223> OTHER INFORMATION: Description of Artificial Sequence: Light chain
      antibody

<400> SEQUENCE: 15
ggtgatccag ttgcacctac tgtcctcatc ttcccaccag ctgctgatca ggtggcaact      60

```
ggaacagtca ccatcgtgtg tgtggcgaat aaatactttc ccgatgtcac cgtcacctgg      120
gaggtggatg gcaccaccca aacaactggc atcgagaaca gtaaaacacc gcagaattct      180
gcagattgta cctacaacct cagcagcact ctgacactga ccagcacaca gtacaacagc      240
cacaaagagt acacctgcaa ggtgacccag ggcacgacct cagtcgtcca gagcttcaat      300
aggggtgact gttag                                                       315
```

```
<210> SEQ ID NO 16
<211> LENGTH: 132
<212> TYPE: PRT
<213> ORGANISM: Artificial Sequence
<220> FEATURE:
<223> OTHER INFORMATION: Description of Artificial Sequence: Light chain
      antibody

<400> SEQUENCE: 16

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Ser Ala Ala Val Gly Gly Thr Val Thr Ile Asn Cys Gln Ala Ser
        35                  40                  45

Gln Ser Ile Ser Asn Leu Leu Ala Trp Tyr Gln Gln Lys Pro Gly Gln
    50                  55                  60

Pro Pro Lys Leu Leu Ile Tyr Ser Ala Ser Thr Leu Ala Ser Gly Val
65                  70                  75                  80

Pro Ser Arg Phe Lys Gly Ser Gly Ser Gly Thr Gln Phe Thr Leu Thr
                85                  90                  95

Ile Ser Asp Leu Glu Cys Ala Asp Ala Ala Thr Tyr Tyr Cys Gln Gln
            100                 105                 110

Gly Tyr Asp Gly Ile Gly Val Val Asn Phe Phe Gly Gly Gly Thr Glu
        115                 120                 125

Val Val Val Lys
    130
```

```
<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Light chain
      antibody fragment

<400> SEQUENCE: 17

Gln Ala Ser Gln Ser Ile Ser Asn Leu Leu Ala
1               5                   10
```

```
<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Light chain
      antibody fragment

<400> SEQUENCE: 18

Ser Ala Ser Thr Leu Ala Ser
1               5
```

```
<210> SEQ ID NO 19
```

```
<211> LENGTH: 12
<212> TYPE: PRT
<213> ORGANISM: Artificial Sequence
<220> FEATURE:
<223> OTHER INFORMATION: Description of Artificial Sequence: Light chain
      antibody fragment

<400> SEQUENCE: 19

Gln Gln Gly Tyr Asp Gly Ile Gly Val Val Asn Phe
1               5                   10

<210> SEQ ID NO 20
<211> LENGTH: 104
<212> TYPE: PRT
<213> ORGANISM: Artificial Sequence
<220> FEATURE:
<223> OTHER INFORMATION: Description of Artificial Sequence: Light chain
      constant region

<400> SEQUENCE: 20

Gly Asp Pro Val Ala Pro Thr Val Leu Ile Phe Pro Pro Ala Ala Asp
1               5                   10                  15

Gln Val Ala Thr Gly Thr Val Thr Ile Val Cys Val Ala Asn Lys Tyr
            20                  25                  30

Phe Pro Asp Val Thr Val Thr Trp Glu Val Asp Gly Thr Thr Gln Thr
        35                  40                  45

Thr Gly Ile Glu Asn Ser Lys Thr Pro Gln Asn Ser Ala Asp Cys Thr
    50                  55                  60

Tyr Asn Leu Ser Ser Thr Leu Thr Leu Thr Ser Thr Gln Tyr Asn Ser
65                  70                  75                  80

His Lys Glu Tyr Thr Cys Lys Val Thr Gln Gly Thr Thr Ser Val Val
                85                  90                  95

Gln Ser Phe Asn Arg Gly Asp Cys
                100
```